(12) United States Patent
Ning

(10) Patent No.: US 6,987,831 B2
(45) Date of Patent: Jan. 17, 2006

(54) APPARATUS AND METHOD FOR CONE BEAM VOLUME COMPUTED TOMOGRAPHY BREAST IMAGING

(75) Inventor: Ruola Ning, Fairport, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/400,915

(22) Filed: Mar. 28, 2003

(65) Prior Publication Data

US 2004/0081273 A1    Apr. 29, 2004

Related U.S. Application Data

(63) Continuation-in-part of application No. 10/291,745, filed on Nov. 12, 2002, now abandoned, which is a continuation-in-part of application No. 09/640,713, filed on Aug. 18, 2000, now Pat. No. 6,480,565.

(60) Provisional application No. 60/166,223, filed on Nov. 18, 1999.

(51) Int. Cl.
*A61B 6/04* (2006.01)

(52) U.S. Cl. ............................................ 378/37; 378/20
(58) Field of Classification Search ................ 378/37, 378/20
See application file for complete search history.

(56) References Cited

U.S. PATENT DOCUMENTS

| 5,526,394 A | * | 6/1996 | Siczek et al. | ................. 378/37 |
| 5,602,891 A | * | 2/1997 | Pearlman | ..................... 378/62 |
| 6,298,114 B1 | * | 10/2001 | Yoda | ........................... 378/37 |

* cited by examiner

*Primary Examiner*—Craig E. Church
(74) *Attorney, Agent, or Firm*—Blank Rome LLP

(57) ABSTRACT

Cone beam volume CT breast imaging is performed with a gantry frame on which a cone-beam radiation source and a digital area detector are mounted. The patient rests on an ergonomically designed table with a hole or two holes to allow one breast or two breasts to extend through the table such that the gantry frame surrounds that breast. The breast hole is surrounded by a bowl so that the entire breast can be exposed to the cone beam. Spectral and compensation filters are used to improve the characteristics of the beam. A materials library is used to provide x-ray linear attenuation coefficients for various breast tissues and lesions.

9 Claims, 22 Drawing Sheets

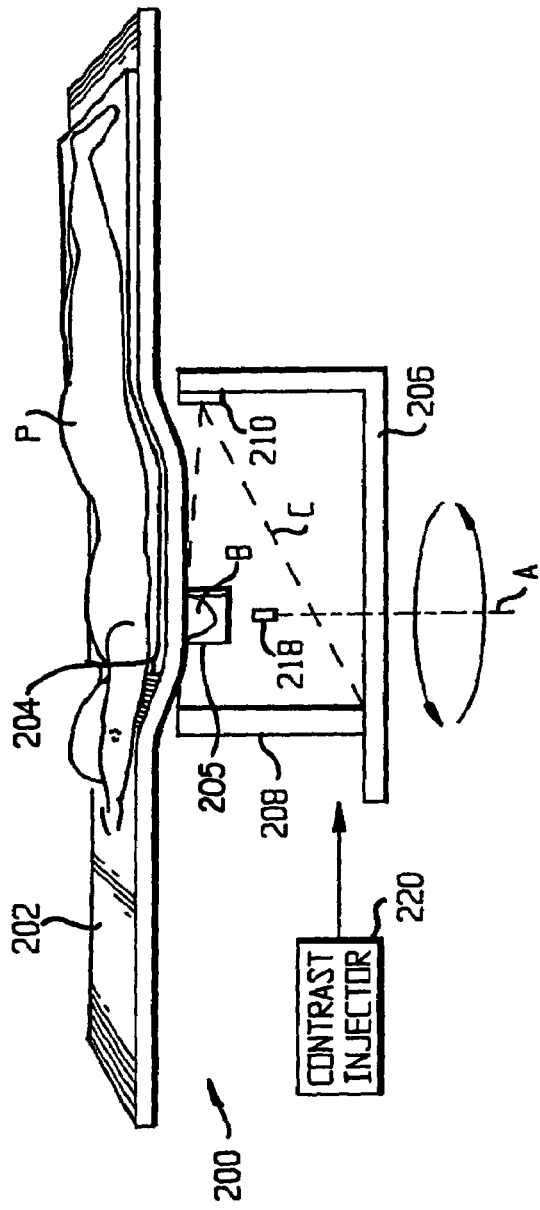
FIG._2A
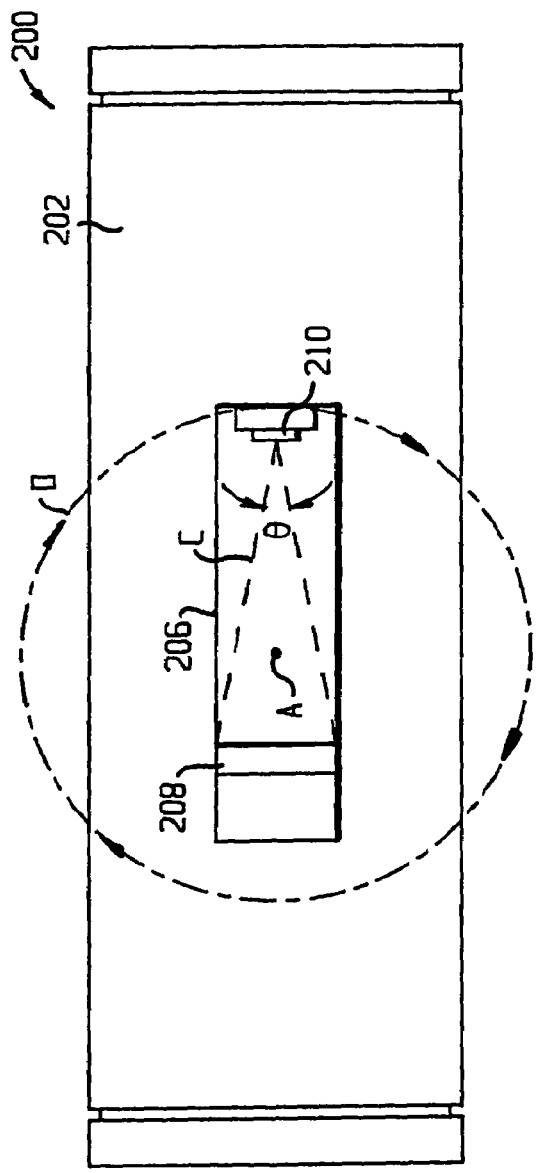
FIG._2B

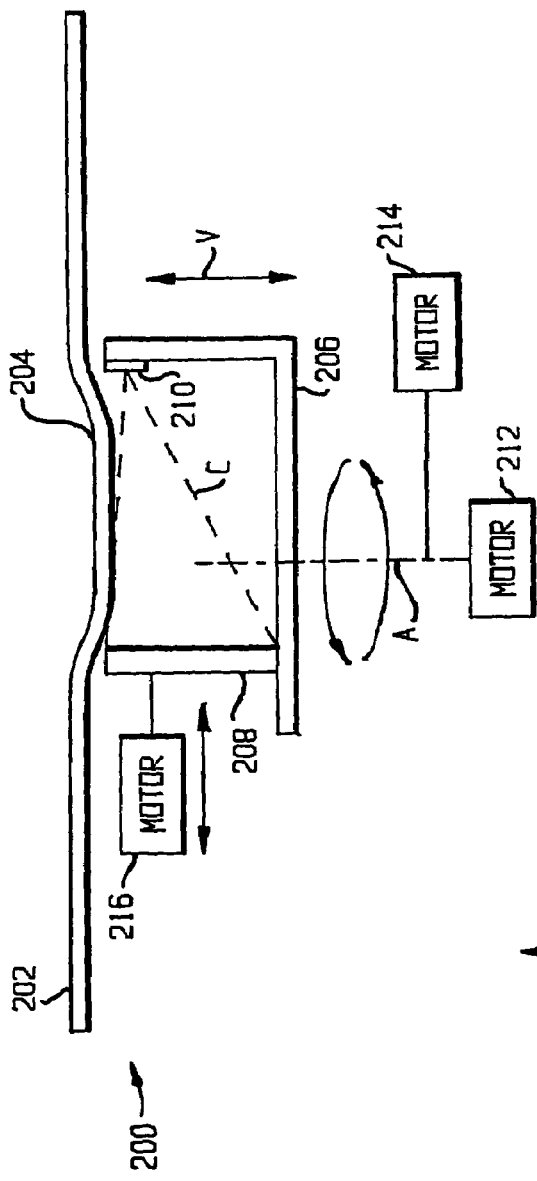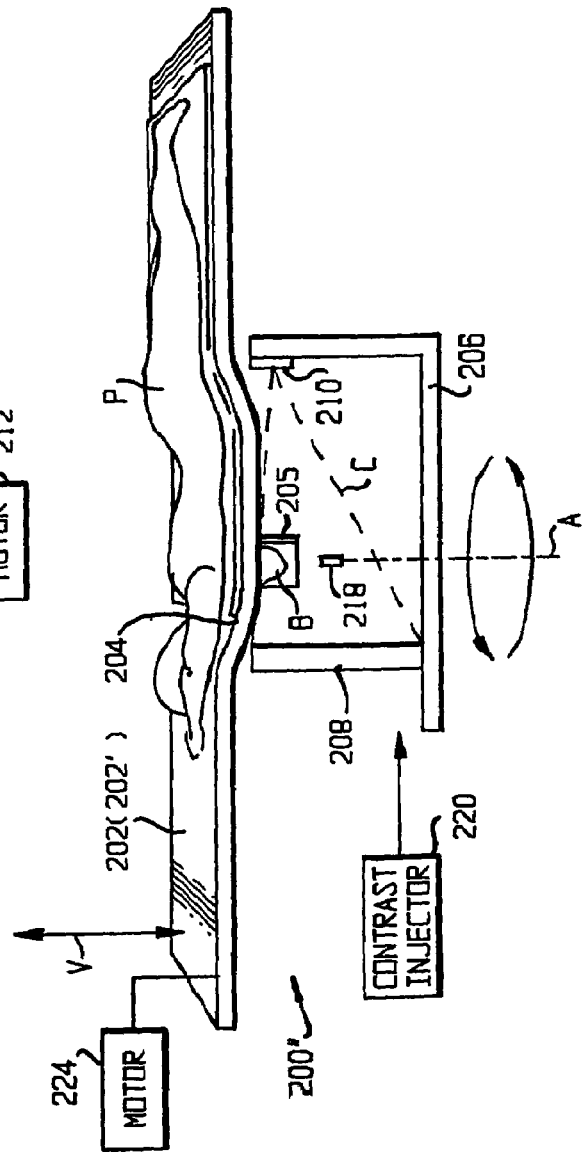

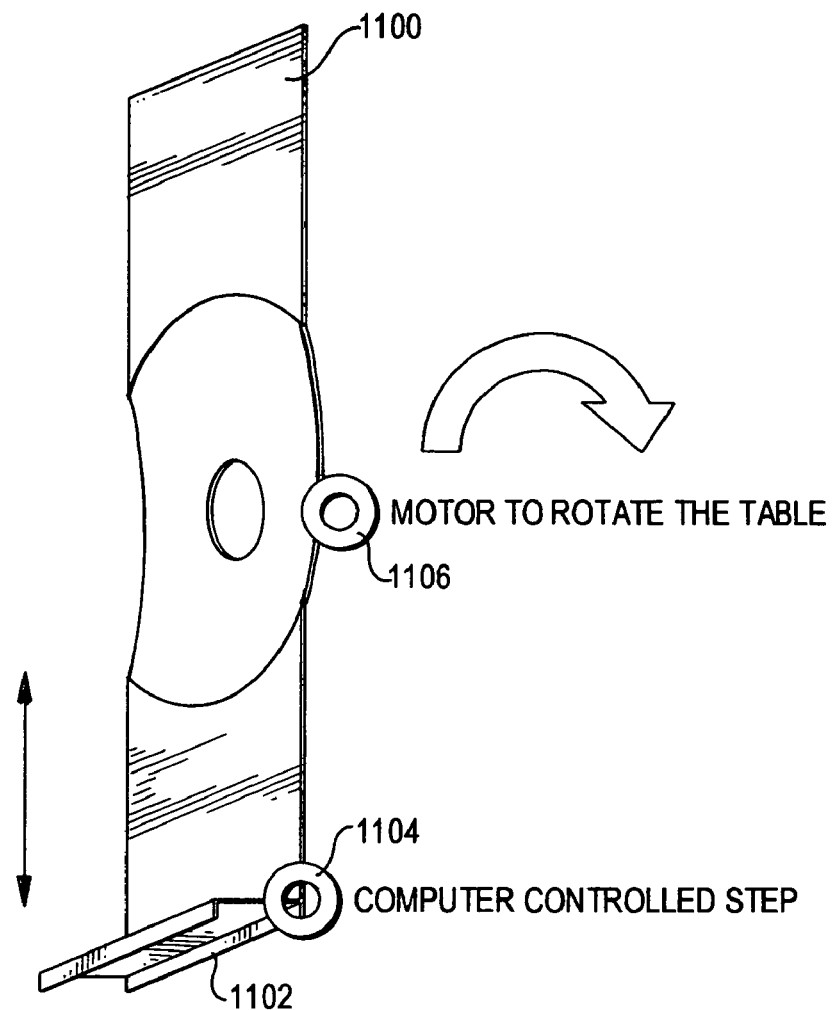
FIG. 11A VERTICAL POSITION
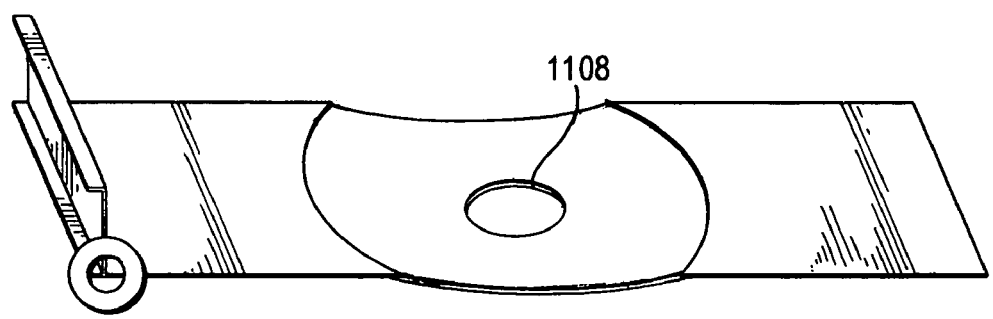
FIG. 11B HORIZONTAL POSITION

360° SCAN ORBIT

PARTIAL SCAN (180 PLUS
CONE ANGLE SCAN ORBIT)

PARTIAL SCAN ORBIT TO
AVOID TO SCAN THE ARM

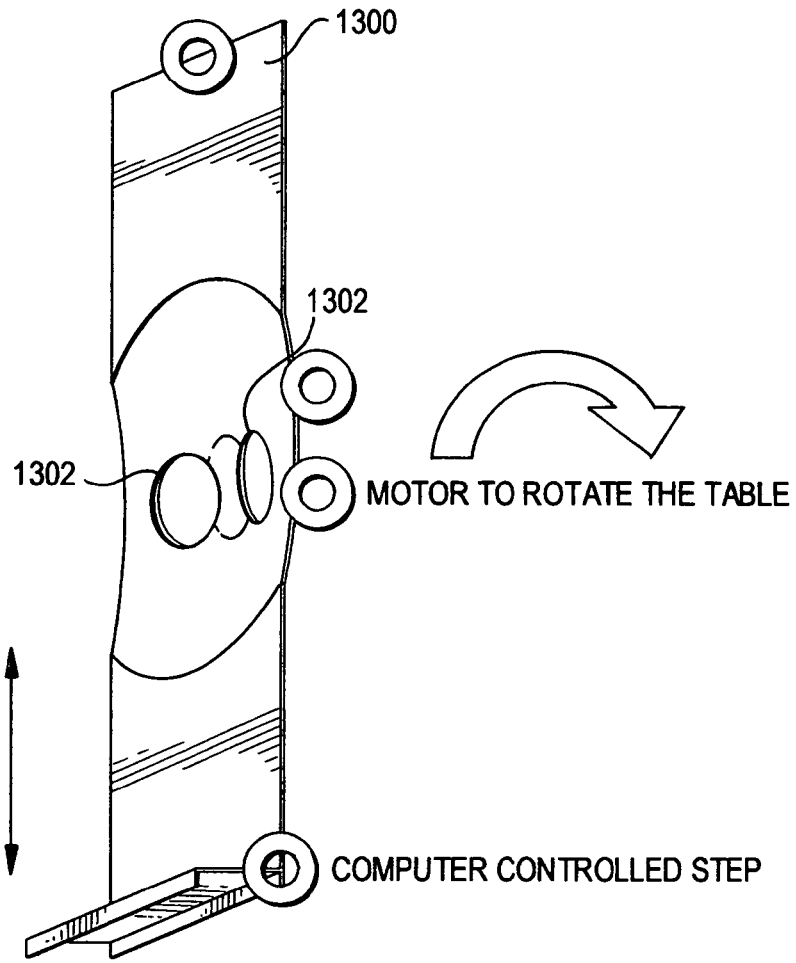
FIG. 13A VERTICAL POSITION
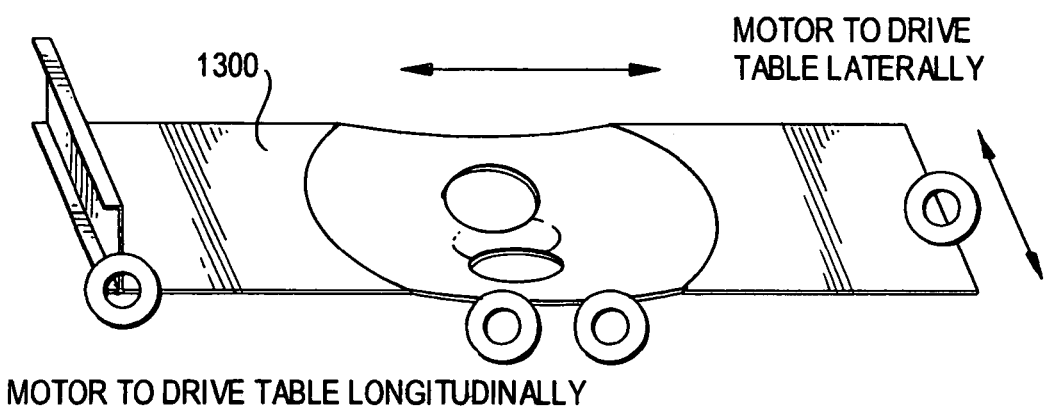
FIG. 13B HORIZONTAL POSITION

VIEW FROM THE BOTTOM OF
THE TABLE SHOWN IN FIG. 13B

VIEW FROM THE BOTTOM OF
THE TABLE SHOWN IN FIG. 14B

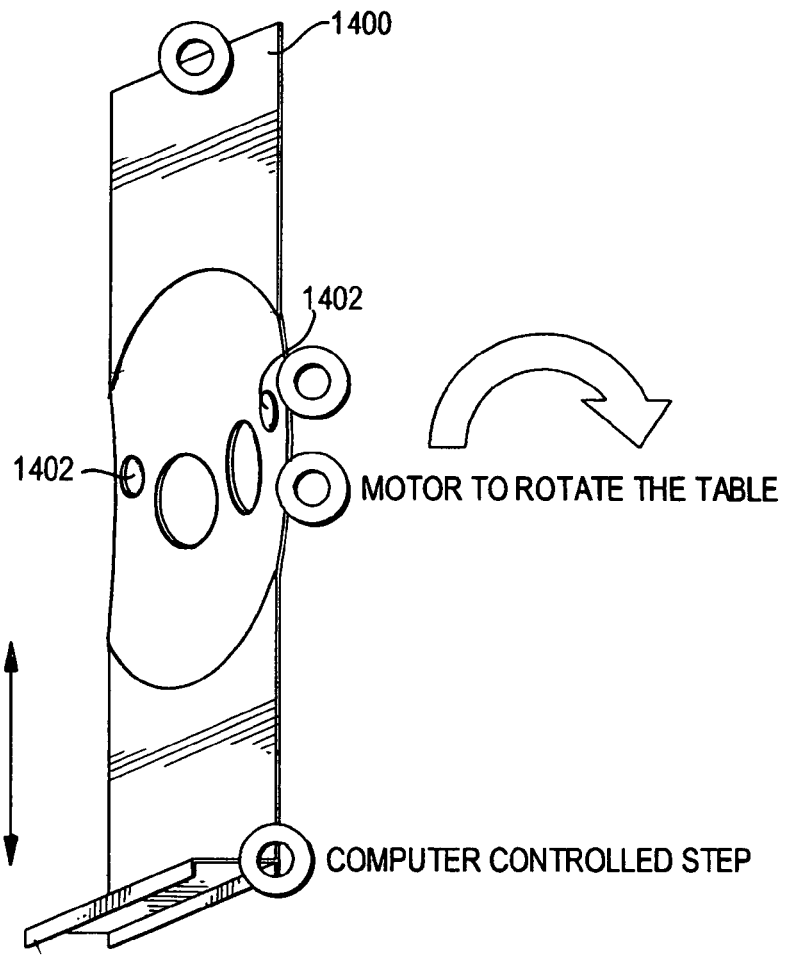
FIG. 14A VERTICAL POSITION
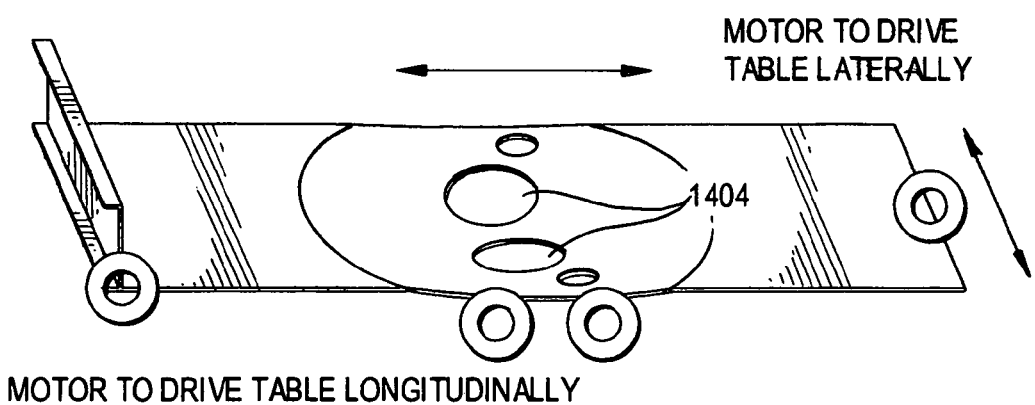
FIG. 14B HORIZONTAL POSITION

APPARATUS AND METHOD FOR CONE BEAM VOLUME COMPUTED TOMOGRAPHY BREAST IMAGING

REFERENCE TO RELATED APPLICATION

This application is a continuation-in-part of U.S. patent application Ser. No. 10/291,745 filed Nov. 12, 2002 now abandoned, which is a continuation-in-part of U.S. patent application Ser. No. 09/640,713, filed Aug. 18, 2000, now U.S. Pat. No. 6,480,565, which claims the benefit of U.S. Provisional Application No. 60/166,223, filed Nov. 18, 1999. The disclosures of all of those applications are hereby incorporated by reference in their entireties into the present disclosure.

BACKGROUND OF THE INVENTION

1. Field of the Invention

The present invention relates to the use of cone beam volume computed tomography (CBVCT) in breast imaging and in particular to improvements therein that make better use of the radiation from the radiation source, the data output by the detector, or both. Throughout the present disclosure, it will be understood that references to breast imaging (mammography) are illustrative rather than limiting, as the invention is broadly applicable to breast imaging in general.

2. Description of Related Art

Breast cancer represents a significant health problem. More than 180,000 new cases are diagnosed, and nearly 45,000 women die of the disease each year in the United States.

The clinical goal of breast imaging is to detect tumor masses when they are as small as possible, preferably less than 10 mm in diameter. It is reported that women with mammographically detected, 1–10 mm invasive breast carcinoma have a 93% 16-year survival rate.

Conventional screen film mammography is the most effective tool for the early detection of breast cancer currently available. However, mammography has relatively low sensitivity to detect small breast cancers (under several millimeters). Specificity and the positive predictive value of mammography remain limited owing to an overlap in the appearances of benign and malignant lesions. Limited sensitivity and specificity in breast cancer detection of mammography are due to its poor contrast detectability, which is common for all types of projection imaging techniques (projection imaging can only have up to 10% contrast detectability). The sensitivity with which conventional mammography can identify malignant tumors in the pre-clinical phase will largely be affected by the nature of the surrounding breast parenchyma. Detection of calcifications will be influenced to a lesser degree by the surrounding tissue. The perception of breast masses without associated calcification, representing the majority of tumors in patients with detected carcinomas, is greatly influenced by the mammographic parenchymal pattern. Thus conventional mammography is often not able to directly detect tumors of a few millimeters due to poor low contrast resolution. Conventional mammography requires ultrahigh resolution (50–100 $\mu$m/pixel) to image microcalcifications to compensate for its poor contrast resolution. Mammography fails to initially demonstrate 30%–35% of cancers. In addition, not all breast cancers detected with mammography will be found early enough to cure. At best, it appears that conventional mammography can reduce the death rate by up to 50%. This is an important gain, but there is considerable room for improvement in early detection of breast cancer.

Relatively low specificity of mammography results in biopsy for indeterminate cases despite the disadvantages of higher cost and the stress it imposes on patients. There is a need for more accurate characterization of breast lesions in order to reduce the biopsy rate and false-positive rate of biopsy.

There are several radiological or biological characteristics of breast carcinoma that can be imaged. First, carcinoma has different x-ray linear attenuation coefficients from surrounding tissues, as shown in FIG. 1. Second, carcinoma has a substantially higher volume growth rate compared to a benign tumor which lacks growth. Third, carcinoma has patterns distinguishable from those of a benign tumor. Fourth, benign tumors show different contrast enhancement after intravenous contrast injection. Fifth, the presence of neovascularity can indicate cancer. Conventional mammography relies mainly on the first characteristic and partially uses the third characteristic for breast cancer detection. Since mammography is a two-dimensional static imaging technique, it cannot provide any information regarding characteristics 2, 4, or 5.

Currently, radiological evaluation of breast cancer is important not only for early detection of disease, but also for staging and monitoring response to treatment. So far, conventional screen film mammography has been shown to be the most cost-effective tool for the early detection of breast cancer currently available. The specificity and positive predictive value of mammography, however, remain limited, owing to an overlap in the appearances of benign and malignant lesions and to poor contrast detectability, which is common for all projection imaging techniques. Projection imaging can have only up to 10% contrast detectability. Biopsy is therefore often necessary in indeterminate cases, despite the disadvantages of higher cost and the stress it imposes on patients. There is therefore a need for more accurate characterization of breast lesions in order to reduce the biopsy rate.

In the last decade, MRI of the breast has gained a role in clarifying indeterminate cases after mammography and/or ultrasound, especially after breast surgery and in detecting multifocal breast cancers. However, the integration of MR into routine clinical practice has been hampered by a number of limitations, including long scanning times and the high cost of MR examinations. Additionally, many patients cannot undergo MR because of MR contraindications (e.g., aneurysm clips, pacemaker) or serious claustrophobia.

Characterization of breast lesions on MR has been based largely on the differential rates of enhancement between benign and malignant lesions. The constant trade-off between spatial and temporal resolution in MR has made it difficult to achieve the spatial resolution necessary for improved lesion detection and characterization.

Standard fan beam computed tomography (CT), including spiral CT, has been evaluated as a potential tool for the characterization of breast lesions. Most previous work has been based on the traditional or helical technique using the whole body scanner. That technique, however, suffers from a number of disadvantages including significantly increased radiation exposure due to the fact that standard CT can not be used to target only the breast, so that the majority of x-rays are wasted on whole body scanning. That leads to relatively low in-plane spatial resolution (typically 1.0 lp/mm), even lower through plane resolution (less than or equal to 0.5 lp/mm in the direction perpendicular to slices), and prolonged volume scanning times, since spiral CT scans the whole volume slice by slice and takes 120 seconds for the whole breast scan. It still takes 15–30 seconds for the latest multi-ring spiral CT for 1 mm/slice and 12 cm coverage.

Ultrasound has poor resolution in characterizing lesion margins and identifying microcalcifications. Ultrasound is also extremely operator dependent.

In addition, for conventional mammography, compression is essential for better low-contrast detectability. However, patients are uncomfortable even though compression may not be harmful to them.

The above-cited parent patent application teaches the use of cone beam volume computed tomography (CBVCT) for breast imaging, called cone beam volume CT breast imaging (CBVCTBI) technique. The patient lies on a table with a breast hole through which the breast to be imaged extends. A gantry frame rotates a radiation source and a detector around the breast. However, because of the relative positioning of the radiation source and the table required to achieve the volume scan, the radiation source may be positioned so low relative to the table that the entire breast may not lie within the cone beam (half cone beam). Also, it would be helpful to compensate for the shape of the breast while minimizing discomfort for the patient and to analyze efficiently the signals corresponding to various kinds of breast tissues and lesions. Furthermore, it would be helpful to increase sensitivity of detecting small breast cancer without raising patient dose levels or to reduce patient dose level without compromising image quality of CBVCTBI.

SUMMARY OF THE INVENTION

It will be readily apparent from the foregoing that a need exists in the art for a breast imaging system and method which overcome the above-noted limitations of conventional techniques.

It is therefore a primary object of the invention to provide a clinically useful three-dimensional imaging technique for accurate detection, diagnostics and treatment planning of breast cancer.

It is another object of the invention to provide a breast imaging technique which can operate with only a single fast volume scanning to provide true three-dimensional (3D) description of breast anatomy with high isotropic spatial resolution and lesion location, while conventional mammography only provides two-dimensional projection images.

It is yet another object of the invention to provide imaging technique to tomographically isolate a breast tumor from the other objects in adjacent planes, consequently eliminate overlap and remove superimposed structures.

It is yet another object of the invention to provide higher contrast resolution compared with conventional mammography and adequate spatial resolution for breast cancer detection.

It is yet another object of the invention to improve the detectability of breast carcinoma (tumors) of a few millimeters in size due to much better low contrast resolution, compared to conventional mammography.

It is yet another object of the invention to provide high resolution volume of interest (VOI) reconstruction mode for target imaging and better characterization of breast tumors three-dimensionally compared with conventional mammography.

It is yet another object of the invention to provide a three-dimensional tomographic reconstruction technique to detect the difference of x-ray linear attenuation coefficients of carcinoma from surrounding tissue. (carcinoma has different x-ray linear attenuation coefficients from surrounding tissue.)

It is yet another object of the invention to provide accurate depiction of breast tumor border pattern for better characterization of breast tumors compared with conventional mammography (carcinoma has distinguishable border patterns from those of a benign tumor).

It is yet another object of the invention to improve specificity in breast cancer detection compared with conventional mammography by allowing more precise measurement of change in lesion volume over relatively short periods of time (carcinoma has a much faster volume growth rate than a benign tumor).

It is yet another object of the invention to increase patient comfort by decreasing the amount of breast compression required.

It is yet another object of the invention to use CBVCTBI image-based volume growth measurement technique (both positive growth and negative growth) to determine malignancy of breast tumors and to monitor the effect of breast cancer treatment (this method can be also used for other malignancies, such as lung cancer).

It is yet another object of the invention to use higher x-ray energies than those used in conventional mammography, for breast imaging to increase penetration, improve image quality and reduce patient radiation dose.

It is yet another object of the invention to perform multi-resolution volume tomographic reconstruction from the same set of projection images to improve the dectectibility of microcacification and breast carcinoma (tumors), better characterize breast tumors, and consequently reduce the total accumulative dose for patient.

It is yet another object of the invention to use a CBVCTBI image-based computer aided detection (CAD) technique to improve the detectibility and characterization of breast carcinoma (tumors).

It is yet another object of the invention to improve sensitivity of breast cancer detection and thereby further reduce mortality of breast cancer by detecting small breast cancers that can not be detected by conventional mammography.

It is yet another object of the invention to improve specificity of breast cancer detection and greatly reduce the biopsy rate.

It is yet another object of the invention to provide a clinically useful dynamic three-dimensional (four-dimensional: three-dimensional space plus time) imaging technique for accurate diagnostics of breast cancer and and greatly reduce the biopsy rate.

It is yet another object of the invention to provide a clinically useful three-dimensional imaging technique for accurate diagnostics by performing contrast injection dynamic studies, and greatly reduce the biopsy rate.

It is yet another object of the invention to provide a clinically useful three-dimensional imaging technique for angiogenesis studies that indicate the neovacularity of breast cancer and improve the efficiency of breast cancer treatment planning by performing contrast injection dynamic studies.

It is yet another object of the invention to provide adequate image quality for the mammographically dense breast.

It is yet another object of the invention to facilitate 3D image-guided biopsy procedures.

It is yet another object of the invention to allow accurate assessment of cancer extent (margin) for both better pre-surgical planning, especially in limited resections, and radiation therapy treatment planning, as well as for more accurate monitoring of breast cancer response to treatments.

It is yet another object of the invention to design the table and the relative placement of the table and the radiation source such that the entire breast or as much of the breast including the chest wall as possible, lies within the cone beam (half cone beam).

It is yet another object of the invention to design the table and the relative placement of the table and the radiation source such that the coverage of the breast near chest wall is equivalent to that of conventional mammography. It is yet another object of the invention to control the beam to take into account the shape of the breast.

It is yet another object of the invention to improve analysis of various kinds of breast tissues and lesions.

It is yet another object of the invention to reduce the required patient dose level (glandular dose level) by incorporating one or both of a spectral filter to provide the appropriate radiation spectrum and beam compensation filter shaped to take into account the shape of the breast.

It is yet another object of the invention to improve the image quality of CBVCTBI (reduce beam hardening artifacts and the dynamic range of the detected x-ray intensities) by incorporating one or both of a spectral filter to provide the appropriate radiation spectrum and beam compensation filter shaped to take into account the shape of the breast.

It is yet another object of the invention to improve the image quality by reducing and correcting for x-ray scatter.

It is yet another object of the invention to facilitate the image-guided surgical and radiation treatments by fusing 2D real time projection image with 3D cone beam reconstructions on line.

It is yet another object of the invention to reduce image noise three-dimensionally and consequently improve the sensitivity of detecting small breast tumors without increasing patient dose level.

It is yet another object of the invention to further reduce patient dose level without compromising the sensitivity of detecting small breast tumors by preserving image noise level nearly unchanged three-dimensionally.

To achieve the above and other objects, the present invention is directed to a system and method incorporating a cone beam volume tomographic reconstruction technique with the recently developed flat panel detector to achieve cone beam volume computed tomography breast imaging (CBVCTBI). With cone beam geometry and a flat panel detector, a flat panel-based CBVCTBI system can be constructed, and three-dimensional (3D) reconstructions of a breast from a single fast volume scan can be obtained. In contrast to conventional mammography, the flat panel-based CBVCTBI system can provide the ability to tomographically isolate an object of interest (e.g., a lesion) from an object (e.g., other lesion or calcification) in adjacent planes. The 3D tomographic reconstructions eliminate lesion overlap and provide a complete, true 3D description of the breast anatomy. In contrast to existing computed tomography (CT) with an intraslice resolution of 1.0 lp/mm and through plane resolution of 0.5 lp/mm, the CBVCTBI reconstructions can have 2.0 lp/mm or better of isotropic spatial resolution (or, more generally, better than 1 lp/mm) along all three axes. The invention is further directed to an ultrahigh resolution volume of interest (VOI) reconstruction using the zoom mode of the flat panel detector to achieve up to 5.0 lp/mm resolution. Thus, CBVCTBI can have many times better contrast detectability (tomographic imaging can have up to 0.3% contrast detectability) than that of conventional mammography.

Various scanning geometries can be used. It is contemplated that either a circle scan or a circle-plus-line (CPL) scan will be used, depending on the size of the breast. However, other geometries, such as spiral, can be used instead.

The present invention provides better detection of breast cancers, better lesion characterization, and more accurate preoperative and postoperative information on breast anatomy, thus reducing the negative biopsy rate.

The present imaging technique has significant clinical impact on breast cancer detection, diagnosis and the evaluation of the effectiveness of therapy. Because of its excellent low contrast detectability and high and isotropic resolution, the present invention significantly improves the accuracy of breast lesion detection, and hence greatly reduces the biopsy rate. The potential clinical applications of such a modality are in the imaging of the mammographically indeterminate lesions, the mammographically dense breast and the post-surgical breast. Currently, most mammographically indeterminate lesions end up being biopsied in order to arrive at a definitive diagnosis. It is well known that the usefulness of mammography in patients with dense breasts is limited and that additional imaging or biopsy is frequently required. The use of an imaging modality that has a capability for multi-planar and volumetric data acquisition has the potential to improve lesion characterization in dense breast tissue. The higher spatial resolution afforded CBVCTBI can potentially improve the differentiation of recurrence and form of post-surgical changes.

The present invention provides very high-resolution tomographic images by zooming in on small lesions or specific regions within a tumor. Detailed interrogation of specific areas within a lesion, e.g., microcalcifications, necrotic and cystic as well as areas of intraductal extension enables more accurate characterization of breast lesions. The use of contrast material and dynamic imaging provides additional temporal information, which, together with morphological features, enhances specificity and reduces the biopsy rate.

Tumor angiogenesis is an independent prognostic indicator in breast cancer. Currently, angiogenesis is determined by assessing microvessel density in pathologic specimens. However, researchers have also detected good correlation between contrast enhancement and microvessel density. The use of contrast medium in an imaging modality that provides very high spatial and temporal resolution offers a non-invasive method to assess tumor angiogenesis. Additionally, the acquisition of volumetric data with 3D rendering allows multiplanar imaging and better presurgical planning, especially in limited resections.

In summary, the introduction of CBVCTBI, with the potential for obtaining a very high spatial resolution tomographic images, offers improved lesion characterization in mammographically indeterminate breast lesions with a view to reducing the biopsy rate. It also offers the advantages of enhancing preoperative and postoperative planning.

CBVCTBI has the capacity to provide information regarding characteristics 1–5 discussed above with reference to the prior art to improve lesion detection and characterization.

In a preferred embodiment, the patient lies face down on an ergonomic patient table having one or two breast holes. The table has a bowl surrounding the breast hole. Thus, the hole is sufficiently low that the entire breast extending from the breast hole can be imaged within the beam of radiation. In a particular design of the table, there is an intermediate depressed portion between the bowl and the rest of the table. That arrangement allows the source to make a complete rotation around the breast while allowing the entire breast to lie within the cone beam.

The gantry holding the x-ray source and the flat panel detector rotates below the table to image the breast or two breasts. To obtain projections other than simple circle projections, the gantry frame can be moved vertically, or the table can be moved vertically. One advantage of having two breast holes is to preserve the geometric relationship between the breasts.

The source can incorporate one or both of a spectral filter to provide the appropriate radiation spectrum and beam compensation filter shaped to take into account the shape of the breast. In a particular embodiment, the thickness of the attenuator at any particular slice is a linear function of the difference between the diameter of the breast at that slice and the maximum diameter of the breast.

The CBVCTBI device outputs three-dimensional cone beam volume CT reconstruction image matrix of a breast. The three-dimensional cone beam volume CT reconstruction image matrix of a breast is a cone beam 3D reconstruction matrix of x-ray linear attenuation coefficient distribution of a breast. For analysis of the signals output by the CBVCTBI scanner, a library of attenuation coefficients of various breast tissues and lesions (e.g. adipose, carcinoma, glandular tissue, base (e.g. mixture of 50% adipose and 50% glandular), and calcification) can be used. For the base material (e.g. mixture of 50% adipose and 50% glandular), the attenuation coefficients can be calculated according to the weighted sum based on the composition percentage and the mass density. To obtain finer data tables of the x-ray linear attenuation coefficients vs. photon energies, spline function-based interpolations and extrapolations are used to compute the x-ray linear attenuation coefficients of breast tissue and lesions under a particular photon energy ranging from 10 to 110 keV.

A further modification of the present invention uses an ultra-high-resolution volume-of-interest (VOI) reconstruction mode to focus on a suspicious lesion. The ultra-high-resolution VOI reconstruction mode is analogous to magnified mammography.

CBVCTBI will provide very high-resolution tomographic images by zooming in on small lesions or specific regions within a tumor. Detailed interrogation of specific areas within a lesion (i.e. microcalcifications, necrosis and cysts as well as areas of intraductal extension without overlap structures) will enable more accurate characterization of breast lesions.

CBVCTBI will potentially provide a non-invasive method to assess tumor angiogenesis. Recent work has established that tumor angiogenesis is an independent prognostic indicator in breast cancer. Currently, angiogenesis is determined by assessing microvessel density in pathologic specimens. However, researchers have also detected good correlation between contrast enhancement and microvessel density. The use of contrast media in an imaging modality that provides very high spatial and temporal resolution may offer a non-invasive method to assess tumor angiogenesis.

To improve the sensitivity of detecting a small breast tumor without increasing x-ray exposure and patient dose, three-dimensional noise reduction techniques can be applied to projection data or cone beam reconstruction data of a breast with the present invention. Three-dimensional noise reduction techniques involve reducing noise level in projection data using 2D digital filters or a 2D or 3D wavelet transform operation prior to cone beam reconstruction, and then performing a cone beam reconstruction. Alternatively, three-dimensional noise reduction can be performed by applying digital filters or a 2D or 3D wavelet transform to cone beam reconstruction data. Wavelet transform related algorithms for reducing noise level (de-noise) can be found in: Chen B and Ning, R, "Cone beam volume CT breast imaging (CBVCTBI): wavelet analysis-based multiresolution reconstruction and de-noise technique," Proc. SPIE 4682:236–244 (2002), S. K. Nath, R. M. Vasu, and M. Pandit, "Wavelet based compression and denoising of optical Tomography data," Optics Commun., 167, 37–46 (1999), M. Jansen and A. Bultheel: "Image de-noising by integer wavelet transforms and generalized cross validation," Medical Physics, 26(4), pages 622–630 (1999). The algorithms in the articles just cited are given as illustrative rather than limiting. Any other suitable algorithms can be used instead. In addition, with the present invention, required x-ray exposure and patient dose can be further reduced without decreasing the sensitivity of detecting small tumors, by applying noise reduction technique.

With the present invention, a CBVCTBI scan can be completed rapidly, and several sets of scans can be performed continuously for dynamic contrast studies and angiogenesis studies.

BRIEF DESCRIPTION OF THE DRAWINGS

A preferred embodiment of the present invention will be set forth in detail with reference to the drawings, in which:

FIGS. 2A–2C show a schematic diagram of a cone beam volume CT breast imaging scanner according to the preferred embodiment;

FIG. 2F shows yet another variation of the scanner of FIGS. 2A–2C;

FIGS. 11A and 11B show a modification of the scanner;

FIGS. 13A–13C show yet another modification of the scanner;

FIGS. 14A–14C show a combination of the modifications of FIGS. 11A–13C; and

DETAILED DESCRIPTION OF THE PREFERRED EMBODIMENT

Figure 1:
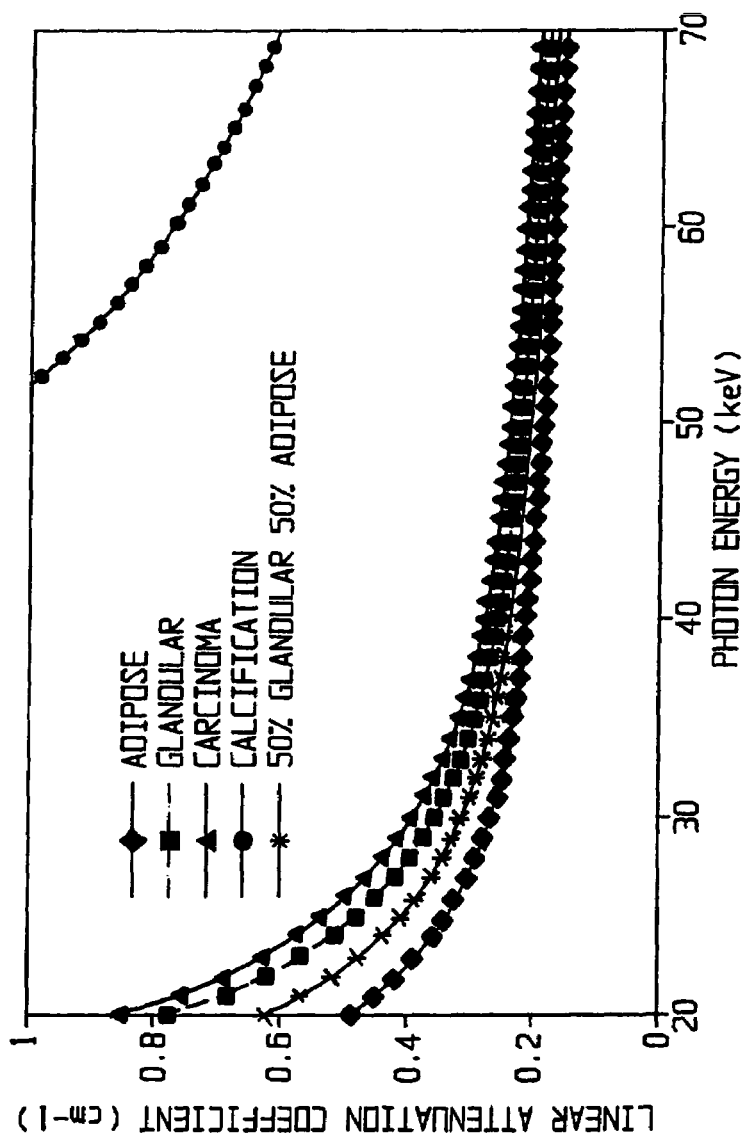
FIG. 1 shows the x-ray linear attenuation coefficients of various tissues which may be found in a healthy or diseased breast.

A preferred embodiment of the present invention and variations thereon will now be set forth in detail with reference to the drawings, in which the same reference numerals refer to the same components throughout.

The limitations accompanying conventional mammography are addressed by incorporating a cone beam volume CT reconstruction technique with a flat panel detector. With cone beam geometry and a flat panel detector, a flat panel-based cone beam volume computed tomography breast imaging (CBVCTBI) system can be constructed as shown in FIGS. 2A–2F, and three-dimensional (3D) reconstructions of a breast from a single fast volume scan can be obtained. In contrast to conventional mammography, the flat panel-based CBVCTBI system provides the ability to tomographically isolate an object of interest (e.g. a lesion) from the other objects in adjacent planes (e.g. other lesion or calcification). The 3D tomographic reconstructions eliminate lesion overlap and provide a complete, true 3D description of breast anatomy. In contrast to conventional computed tomography (CT) with an intraslice resolution of ~1.0 lp/mm and through plane resolution of 0.5 lp/mm, the CBVCTBI reconstructions can have 2.0 lp/mm or better of isotropic spatial resolution. An ultrahigh resolution volume of interest (VOI) reconstruction can be produced by using the zoom mode of the flat panel detector to achieve up to 5.0 lp/mm or better resolution, depending on the size of x-ray focal spot and inherent detector resolution.

An FPD-based CBVCTBI can be built with slip ring technology. A slip ring is an electromechanical device allowing the transmission of electrical power, signals or both across a rotating interface. One source of slip rings is Fabricast, Inc., of South El Monte, Calif., U.S.A.

The schematic design of the CBVCTBI scanner is shown in FIGS. 2A–2F. The CBVCTBI scanner has an ergonomic patent table design and scanning geometry especially suitable for target imaging.

In the scanner 200, the patient P rests on an ergonomically formed table 202 so that the breast B to be scanned descends through a hole 204 in the table 202 into a breast holder 205. The breast holder 205, which will be described in greater detail below, forms the breast B into a cylindrical shape for scanning, which is more comfortable for most patients than the conventional flattened shape. To ensure the appropriate coverage of the chest wall of a breast, it is preferred that at least the left hand of the patient P be put downward aside the body on the table when the left breast of the patient P is scanned, and at least the right hand of the patient P be downward aside the body on the table when the right breast is scanned, respectively. Below, various modifications of the table to facilitate such placement will be disclosed. The table 202 will be explained in detail below with reference to FIGS. 2G and 2H.

Below the table 202, a gantry 206 supports a detector 208 and an x-ray tube 210, one on either side of the breast holder 205. The gantry is turned by a motor 212 to be rotatable around an axis A passing through the breast holder 205, so that as the x-ray tube travels along an orbit O, the breast B remains in the path of a cone beam C emitted by the x-ray tube 210. The gantry is also movable by a motor 214 to go up and down along a vertical path V. Alternatively, the table 202 can be moved up and down along a vertical path V. The detector 208 can be moved toward and away from the axis A by a motor 216 to change the magnification factor if necessary.

To assure the geometric reproducibility of breast imaging and proper imaging of the chest wall, the breast holder 205 is relatively rigid and is made of a material with low x-ray attenuation. The breast holder is shown as being part of the table 202, but it can alternatively be made part of the gantry 206. The breast holder 205 pulls the breast out of the chest wall to assure proper imaging of the chest wall and applies a light and reproducible compression to form the breast into a cylindrical shape. There may be a cushion inside the breast holder to assure the patient's comfort. Then a piston 218 may be used to push the nipple toward the chest wall to reduce z-direction coverage by a couple of centimeters. That piston-pushing reduces the required cone angle of the x-ray beam. Consequently, with the piston-pushing, the majority of breast scans (for breasts <12 cm in height) may be achieved by using only the circular scan mode, and for a large breast, the number of required line projections may be reduced. In addition, the piston-pushing improves uniformity of breast thickness, and consequently improves the uniformity of glandular dose distribution and glandular dose level around the lip of a breast.

A contrast injector 220 can be provided for contrast enhanced tomographic imaging, angiogenesis studies and some other dynamic contrast studies. Various contrast injection media, such as iodine, are known in the art. It is not always necessary to inject a contrast medium into the patient P.

Figure 2D:
FIG. 2D shows one variation of the scanner of FIGS. 2A–2C.

The table 202 can be replaced with the table 202' of FIG. 2D. The table 202' is formed like the table 202, except that two breast holes 204 are provided, each with a breast holder 205. The table 202' is movable. One breast is moved into the imaging field and is scanned first. Then the other breast is moved into the imaging field and scanned. Thus, the geometric relationship between the breasts is preserved. Alternatively, two breasts with two breast holders can be scanned together.

Figure 2E:
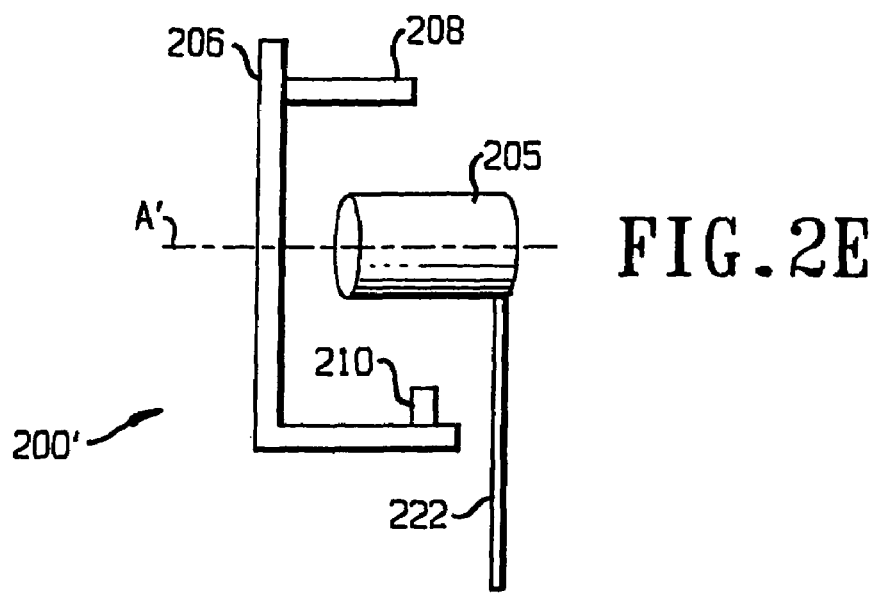
FIG. 2E shows another variation of the scanner of FIGS. 2A–2C.

Alternatively, the scan or scans can be performed while the patient P is standing. As shown in FIG. 2E, in such a scanning system 200', a breast holder 205 is supported by a stand 222 to support a breast of a standing patient P. Alternatively, two breast holders 205 can be provided on the stand 222. One breast is moved into the imaging field and is scanned first. Then the other breast is moved into the imaging field and scanned. Alternatively, two breasts with two breast holders can be scanned together. The gantry 206, holding the detector 208 and the x-ray tube 210, is oriented to rotate around a horizontal axis A' rather than the vertical axis A of FIGS. 2A–2C. In other respects, the system 200' can be like the system shown in FIGS. 2A–2C.

Still another variation is shown in FIG. 2F. The scanner 200" of FIG. 2F is based on either of the scanners 200 and 200' of FIGS. 2A–2E, except that the motor 214 is replaced by a motor 224 to move the table 202 or 202' up and down along the vertical path V. In that way, the gantry 206 does not have to move vertically.

The table 202 will now be explained in detail with reference to FIGS. 2G–2J. The table as shown in those two figures is designed to expose as much of the breast as possible to the imaging radiation without interfering with the data acquisition geometry.

Figure 2G:
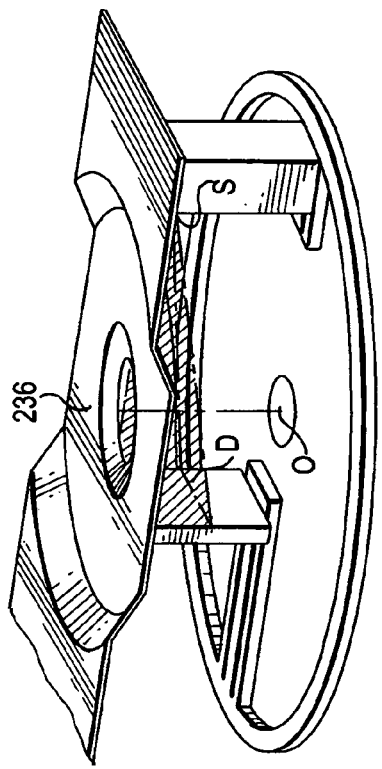
FIGS. 2G and 2H show a first variation of the table used in the scanner of FIGS. 2A–2C.
Figure 2H:
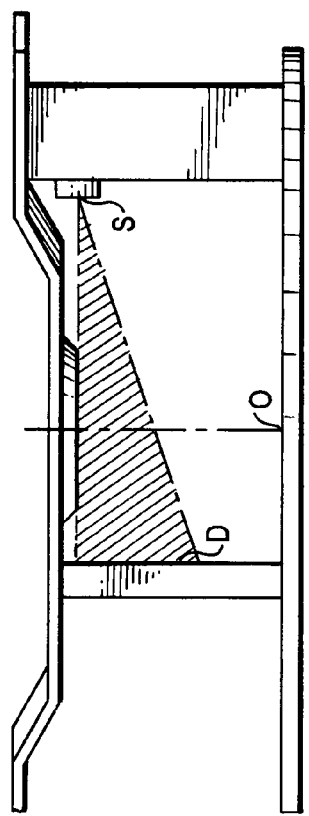

FIGS. 2G–2J show a redesign of the prototype that incorporates two different geometries and scan protocols. The first design, as shown in FIGS. 2G and 2H, is for a 212° (a 180° plus cone angle) scan. The table 202" has a bowl 232 surrounding the breast hole 204. The bowl 232 has a depth of approximately 25 mm and a diameter of approximately 446 mm. Because there is 7 cm between the focal spot and the top of the housing (Varian Rad-71 with MamRad100 Housing), the selected x-ray tube will be sufficiently raised to eliminate any dead space between its central beam and the bottom edge of the ergonomically-designed patient table 202". The x-ray tube will rotate 212° around the breast beyond the sides and superior end of the table. Also, the Varian PaxScan 2520 housing can be modified such that the dead space of the detector will be reduced from the current 3.75 cm to ~2 cm. The table surrounding the breast through-hole will bevel up slightly in a beveled area 234 to accommodate the remaining dead space of the detector housing as it rotates beneath the table so that the top of its active area coincides with the central beam of the x-ray source. With this new design, the chest wall coverage will be equivalent to that of a standard biopsy system with the tube and the detector rotating 212°.

Figure 2I:
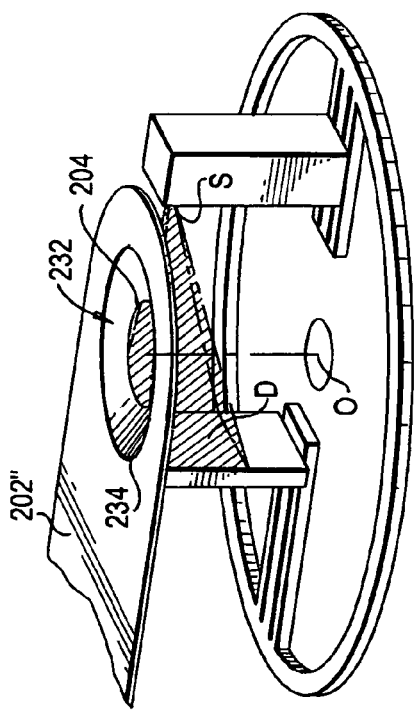
FIGS. 2I and 2J show a second variation of the table used in the scanner of FIGS. 2A–2C.
Figure 2J:
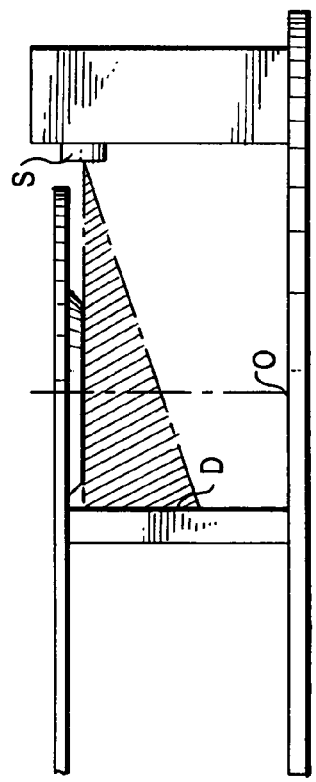

The second design would include a redesign of the patient table-top and a change to the source-to-image distance of the x-ray tube and detector, as shown in FIGS. 2I and 2J. These changes use a beveled intermediate area 236 which will allow the tube/detector assembly to continuously rotate under the table while minimizing any dead space of those components. Also with this design, the chest wall coverage should be equivalent to that of a standard biopsy system with the x-ray tube and the detector continuously rotating 360°. This scan geometry will be particularly effective for fast dynamic studies.

Figure 2K:
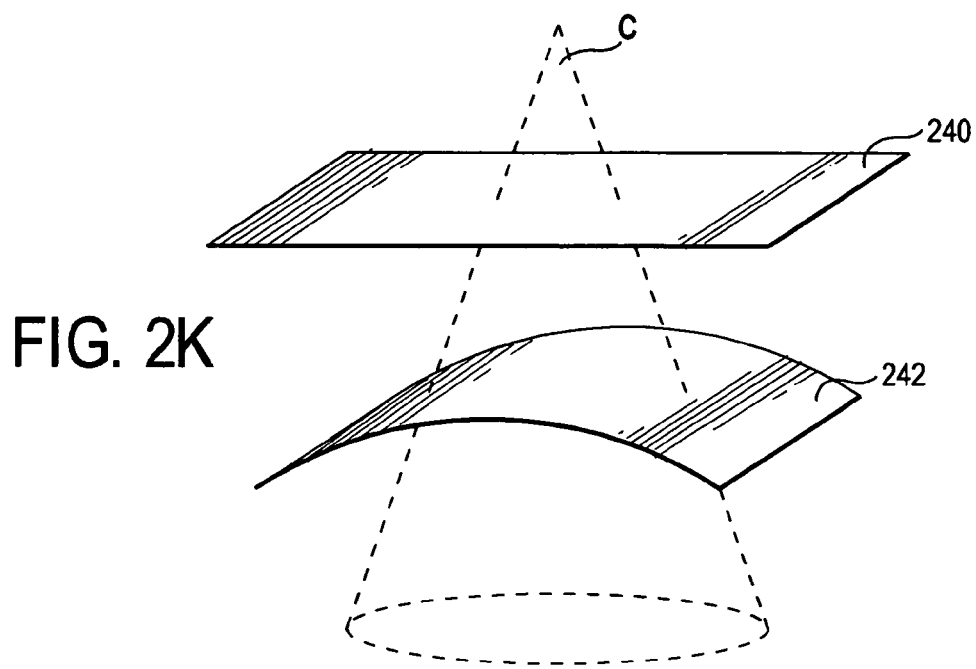
FIG. 2K shows a spectral filter and a compensation filter usable in the scanner of FIGS. 2A–2C.

FIG. 2K shows in greater detail the configuration of the source and detector. To improve the characteristics of the beam, two filters are used. The spectrum filter 240, with selected materials and proper material thickness, forms the optimized spectral shape of entrance x-ray photons at a certain kVp. The beam compensation filter 242, with a designated shape, produces the proper entrance photon flux distributions determined by the varying breast thickness from the chest wall to the tip of the nipple. For an uncompressed or slightly compressed breast, the diameter of a transverse slice changes from the maximum value (e.g. 12 cm) to 0 as the transverse slice position reaches the tip of nipple from the chest wall. To obtain a constant SNR of lesions in the reconstruction image, the beam compensation filter 242 is used. Here the beam compensation filter is a thickness-variant x-ray beam filter (e.g. aluminum or other appropriate materials), whose thickness is linearly proportional to $d_{max}-d$, where $d_{max}$ is the slice diameter (e.g. 12 cm) of the breast at the chest wall, insuring that the resultant projection images are flat.

Figure 3:
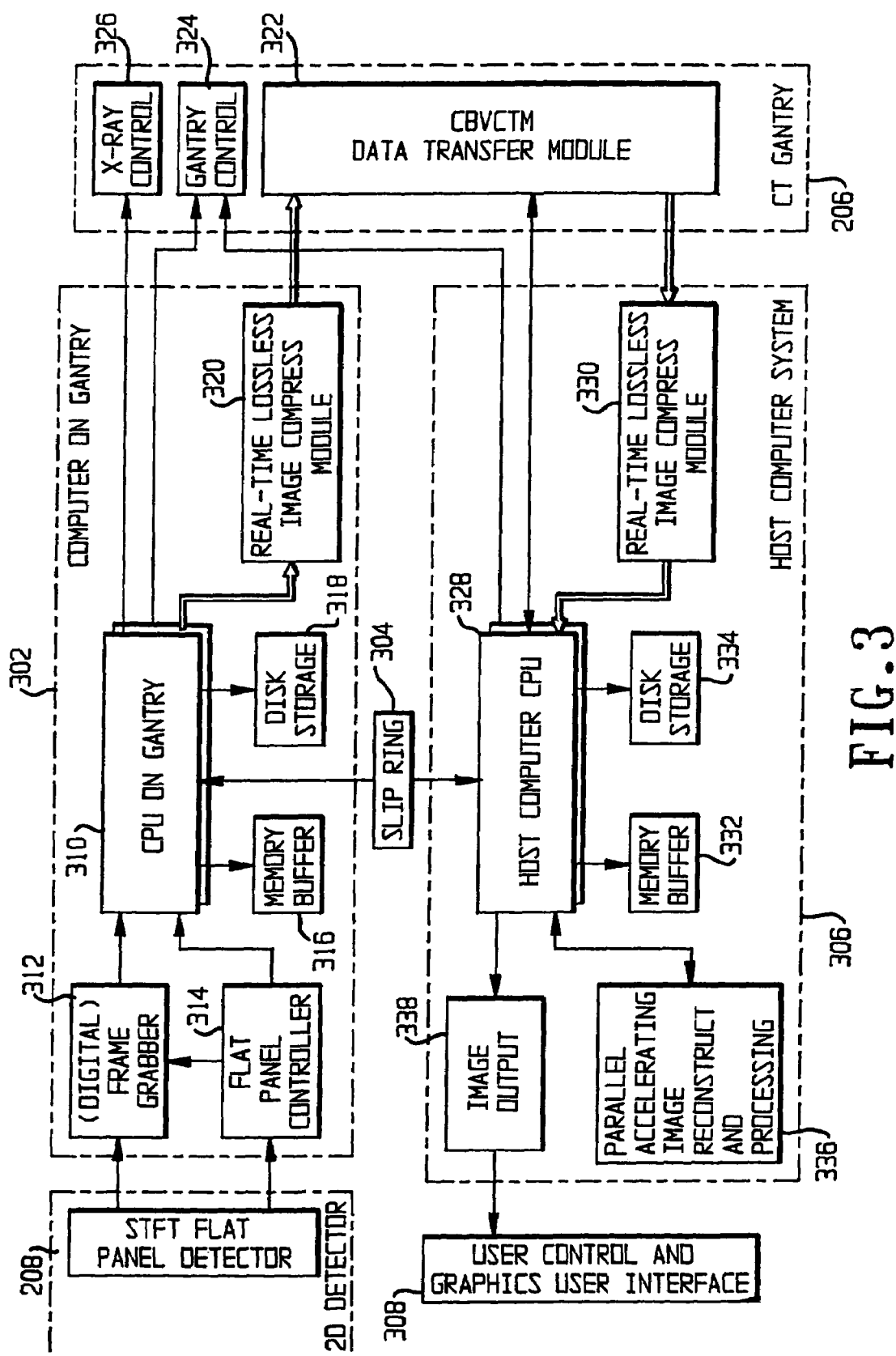
FIG. 3 shows a block diagram of the circuitry used in the scanner of FIGS. 2A–2F.

The circuitry of the scanner 200 is shown in FIG. 3. A computer 302 on the gantry 206 is connected through a slip ring 304 on a shaft of the gantry 206 to a host computer system 306. The computer 302 on the gantry 206 is also in communication with the detector 208, while both computers 302 and 306 are in communication with various other devices on the gantry 206, as explained below. The computer 306 is further in communication with a user control and graphics user interface 308.

In the computer 302 on the gantry 206, the CPU 310 is in communication with the detector 208 through a digital frame grabber 312 and a flat panel controller 314. The CPU 310 is also in communication with a memory buffer 316, disk storage 318 and a real-time lossless image compression module 320; through the compression module 320, the CPU 310 communicates with a CBVCTBI data transfer module 322 on the gantry 206. The CPU 310 directly communicates with two other devices on the gantry, namely, the gantry control 324 and the x-ray control 326. The x-ray control 326 can control the exposure pulse length, exposure timing, and exposure pulse numbers. In addition, the x-ray control 326 can real-timely (dynamically) change x-ray exposure level from projection to projection to achieve optimal x-ray dose efficiency without degrading reconstructed image quality.

In the host computer system 306, a host computer CPU 328 communicates with the data transfer module 322, both directly and through a real-time image decompression module 330. The CPU 328 is also in communication with a memory buffer 332, disk storage 334 and a parallel accelerating image reconstruction and processing module 336. Through an image output 338, the CPU 328 communicates with the interface 308. The CPU's 310 and 328 communicate with each other through the slip ring 304. Also, although it is not shown in FIG. 3 for simplicity, all communication between components on the gantry 206 and the host computer system 306 take place through the slip ring 304.

The CPU 328 with the Parallel Accelerating Image Reconstruction and Processing Module 336 can perform multi-resolution volume tomographic reconstruction from the same set of projection images to improve the detectability of microcalcification and breast carcinoma (tumors), better characterize breast tumors and consequently reduce the total accumulative dose for the patient P. The CPU 328 can also be used in a CBVCTBI image-based computer aided diagnosis technique to improve the detectability and characterization of breast carcinoma.

The slip ring 304 and a fast gantry 206 permit optimal CPL scanning with a quasi-spiral scanning scheme and fast dynamic contrast studies. With that design, a CBVCTBI scan can be completed within a few seconds, and several sets of scans can be performed continuously for dynamic contrast studies and angiogenesis studies. If the locus of an x-ray source and a detector is a single circle during cone beam scanning (single circle cone-beam geometry), an incomplete set of projection data is acquired. The incompleteness of the projection data results in some unavoidable blurring in the planes away from the central z-plane and resolution loss in the z direction. Using Feldkamp's algorithm which is based on a single circle cone beam geometry, the magnitude of the reconstruction error due to the incompleteness of projection data is increased with cone angle. Computer simulation indicates that for breast imaging and an average breast size (10 cm in height or smaller), the reconstruction error is relatively small (<5%), and no streak artifacts can be observed. A modified Feldkamp's algorithm is used for small and average breast sizes (<12 cm in height), and a circle-plus-lines (CPL) cone beam orbit and its corresponding filter backprojection algorithm are used for a large breast (>12 cm in height). That approach practically solves the problem of the incompleteness of projection data from a single circle cone beam geometry for CBVCTBI scanning. A suitable modified Feldkamp's algorithm is taught in Hu, H., "A new cone beam reconstruction algorithm and its application to circular orbits," SPIE 1994; 2163:223–234. A suitable algorithm for circle-plus-a line is taught in Hu, H., "Exact regional reconstruction of longitudinally-unbounded objects using the circle-and-line cone beam tomographic," Proc. SPIE, Vol. 3032, pp. 441–444, 1997; and in Hu, H., "An improved cone-beam reconstruction algorithm for the circular orbit," Scanning 1996, 18:572–581. Modifications of those known algorithms which can be used in the present invention are taught in the following references: Wang X. and Ning R., "A cone beam reconstruction algorithm for a circle-plus-an arc acquisition geometry," IEEE Trans Med Imag, 1999:vol. 18(9), 815–824 and Tang X and Ning R "A cone beam filtered back-projection (CB-FBP) reconstruction algorithm for a circle-plus-two-arc orbit," Med. Phys. 28 (6):1042–1055, (2001). The algorithms in the articles just cited are given as illustrative rather than limiting. Any other suitable algorithms can be used instead.

Figure 4:
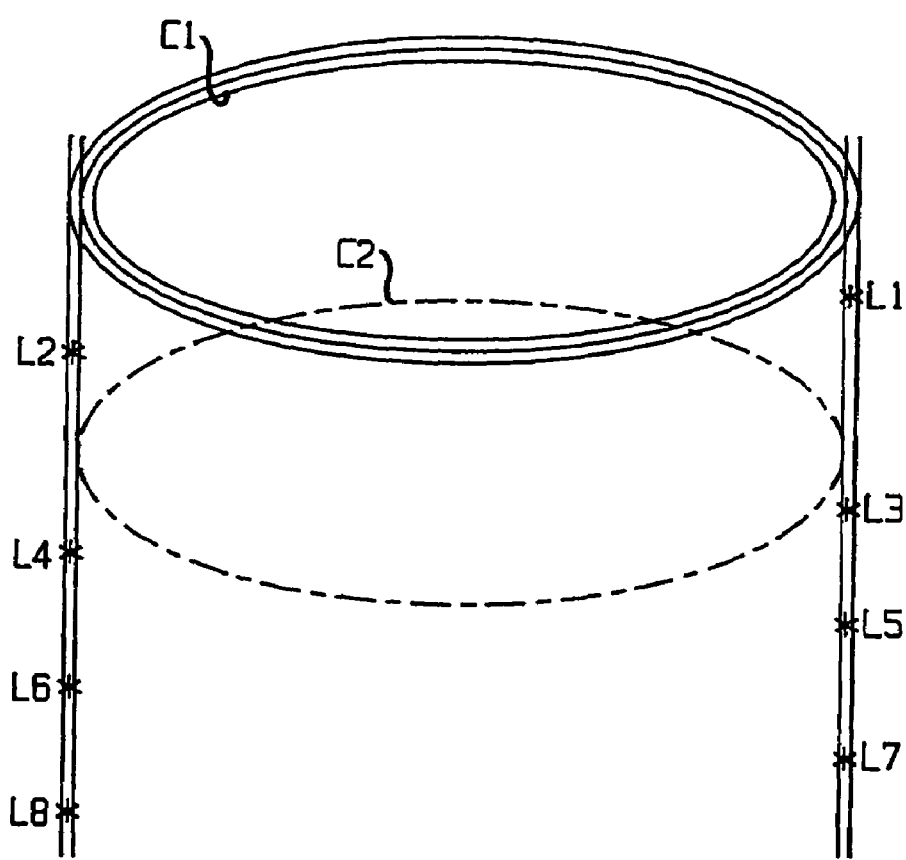
FIG. 4 shows a scanning geometry which can be implemented in the scanner of FIGS. 2A–2F.

The circular scan can be implemented with the CBVCTBI scanner in the following manner: 1) position the patient P's breast B into the hole 204 in the patient table 202 with a lightly-compressed breast holder 205 to form the breast into a cylinder-like shape; 2) rotate the gantry 206 to acquire a set of circle projections over 180° plus cone angle (e.g., 212°, as noted above), or over N×360°, where N is a positive integer (1, 2, 3 . . . ). The CPL scan can be implemented using a quasi-spiral scan with slip ring technology in the following three steps: 1) position the patient P's breast B into the hole 204 in the patient table 202 with a lightly-compressed breast holder 205 to form the breast into a cylinder-like shape; 2) rotate the gantry 206 to acquire a set of circle projections; and 3) once the circle projection is completed, control the gantry 206 to move down and rotate (Alternatively, in the embodiment of FIG. 2F, the patient table 202 can be moved up while the x-ray source 210 and the detector 208 together are rotating), taking projections only at rotation angles 0° and 180° to acquire two line projections per rotation. It is anticipated that multiple line projections are needed to reconstruct a rather large size breast. FIG. 4 shows circular orbits C1 and C2 and positions L1, L2, L3, L4, L5, L6, L7 and L8 at which line projections are taken during one possible scan. Thus, a quasi-spiral implementation of a circle-plus-lines geometry can be provided. The key advantage of quasi-spiral implementation of a circle-plus-lines geometry is to reduce the transition time between line projection acquisition and circle projection acquisition.

Also, in a 180 degrees plus cone beam angle scan, the gantry rotates on orbit C1 or C2 over a total angle of 180 degree plus the size of cone beam angle, which is shown in FIG. 2B as θ. In a 360-degree scan or an N×360 degrees scan, the gantry moves around orbit C1 or C2 the appropriate number of times. A suitable reconstruction algorithm is taught in: Hu, H., "A new cone beam reconstruction algorithm and its application to circular orbits," SPIE 1994; 2163:223–234. A suitable algorithm for circle-plus-a line is taught in Hu, H., "Exact regional reconstruction of longitudinally-unbounded objects using the circle-and-line cone beam tomographic," Proc. SPIE, Vol. 3032, pp. 441–444, 1997; and in Hu, H., "An improved cone-beam reconstruction algorithm for the circular orbit," Scanning 1996, 18:572–581. Modifications of those known algorithms which can be used in the present invention are taught in the following references: Wang X. and Ning R., "A cone beam reconstruction algorithm for a circle-plus-an arc acquisition geometry," IEEE Trans Med Imag, 1999:vol. 18(9), 815–824 and Tang X and Ning R "A cone beam filtered back-projection (CB-FBP) reconstruction algorithm for a circle-plus-two-arc orbit," Med. Phys. 28 (6):1042–1055, (2001). The algorithms in the articles just cited are given as illustrative rather than limiting. Any other suitable algorithms can be used instead. The reader's attention is directed to U.S. Pat. Nos. 5,999,587, 6,075,836, 6,298,110, 6,477,221, and 6,480,565, all by the present inventor.

Figure 7A:
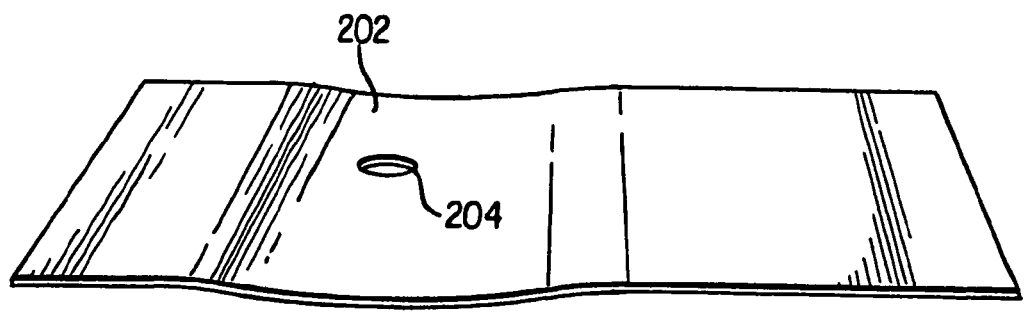
FIGS. 7A–7G show steps in the operation of the device of FIGS. 2A–2F.
Figure 7B:
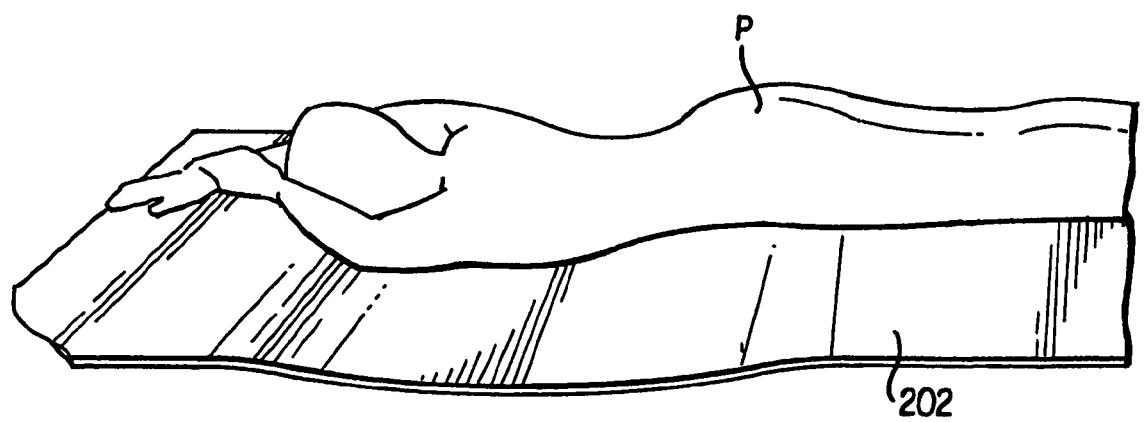
Figure 7C:
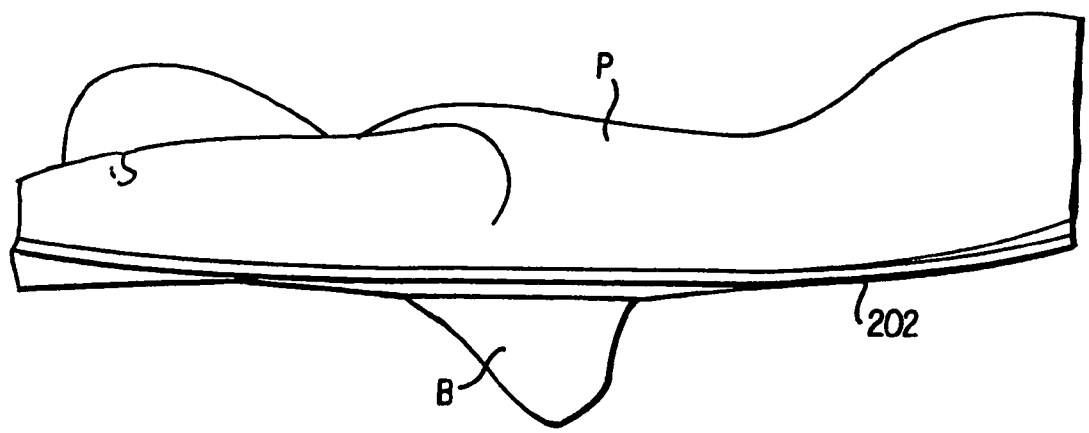
Figure 7D:
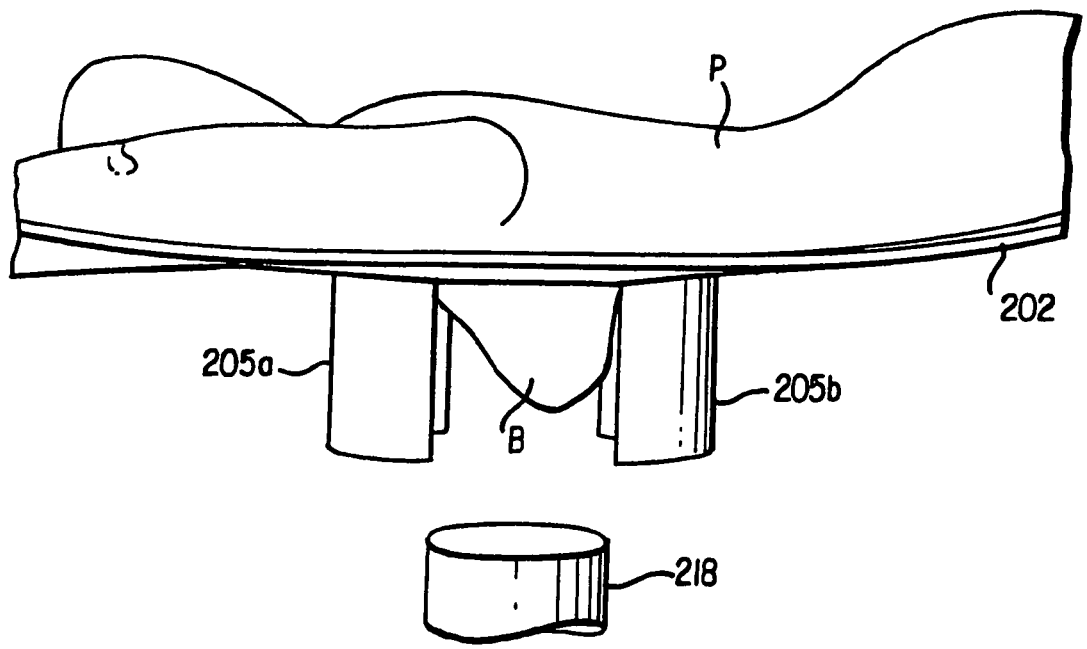
Figure 7E:
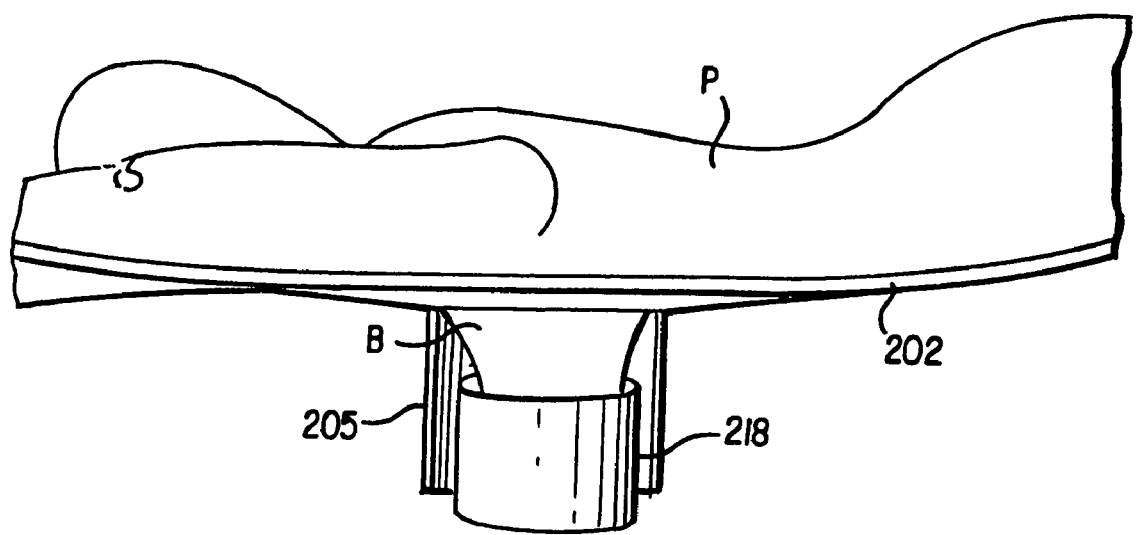
Figure 7F:
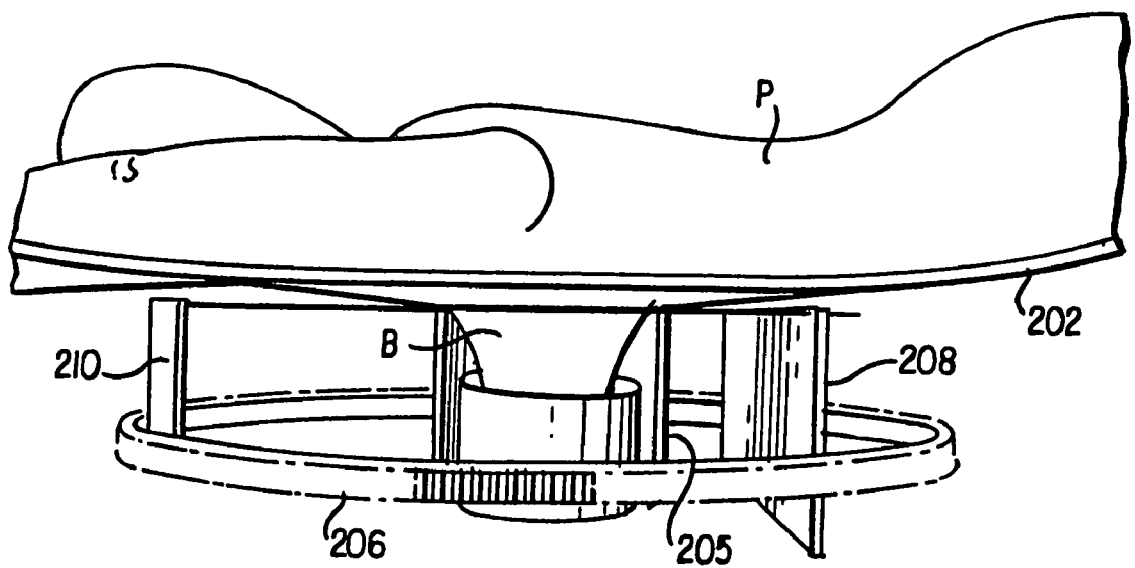
Figure 7G:
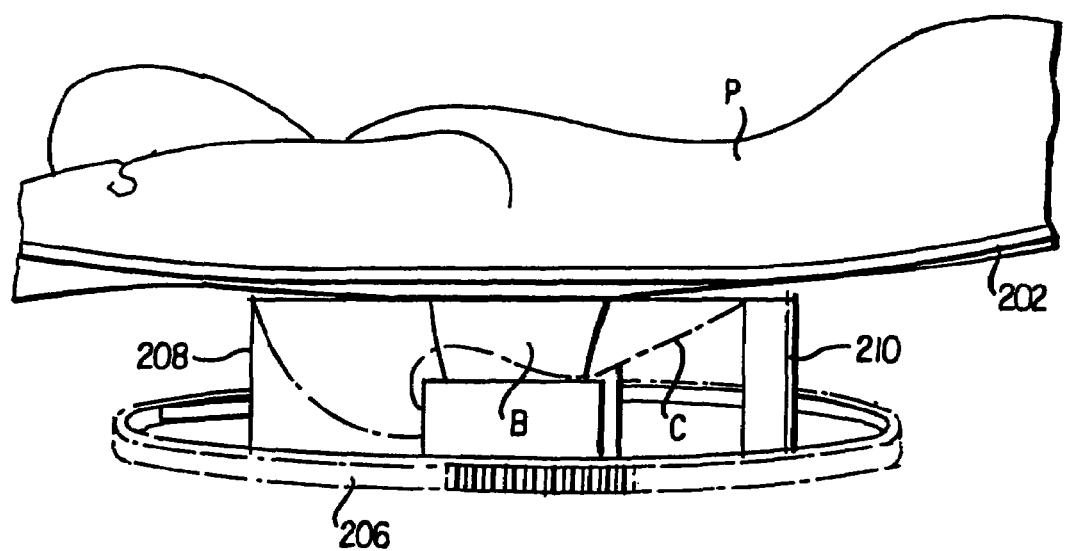

FIGS. 7A–7G show examples of the above steps. FIG. 7A shows the ergonomic table 202 with the breast hole 204. In FIGS. 7B and 7C, the patient P is lying on the table 202 with one breast B extending through the hole 204. In FIG. 7D, the breast holder 205, which is provided in two halves 205a and 205b, is placed around the breast B, and the piston 218 is placed under the breast B. In FIG. 7E, the two halves 205a and 205b of the breast holder 205 and the piston 218 are brought together to compress the breast B into the desired cylindrical shape. In FIG. 7F, the gantry 206, carrying the detector 208 and the x-ray tube 210, is placed in position around the breast B. In FIG. 7G, the gantry 206 is rotating, and the breast B is imaged by a cone beam C emitted by the x-ray tube 210. Any of the embodiments of FIGS. 2A–2F can be used in that manner.

There exist filtered backprojection cone beam reconstruction algorithms based on a circular cone beam orbit and a CPL orbit. Examples have been cited above. Such algorithms are not only computationally efficient but also able to handle a longitudinal truncation projection problem.

Unlike conventional mammography, which required hard breast compression to achieve proper image quality (with which many patients complain about pain), CBVCTBI does not require hard breast compression but prefers a cylindrical formation to improve the geometric reproducibility of 3D-breast imaging. Without hard compression, the maximum thickness of the breast for CBVCTBI is much larger, compared to that of conventional mammography. To achieve maximal object contrast in conventional mammography, it is desired to use very low kVp to achieve effective energies ranging from 17–23 keV, as seen from the attenuation curves of FIG. 1. While this works optimally for a compressed average size breast, using such a low kVp does not work optimally for a compressed large dense breast. This suggests that using such low effective energies (17–23 keV) will not provide enough penetration for an uncompressed breast in a CBVCTBI scan. In addition, from Table 1 below, it can be seen that CBVCTBI has a much wider working energy zone. Therefore, there is much more room to make trade-offs among contrast, dose and x-ray system power output (see Table 1). We require a few hundred very short exposures in one scan. During CBVCTBI imaging, the optimal kVp range and anode-filter combination are selected in order to achieve the best dose efficiency. Computer simulation indicates that the optimal effective energy range is 33–40 keV for an average uncompressed breast.

TABLE 1

Calculated Object Contrast of Cacinoma in Projection Image and CT Image

| Proj. Image | Proj. Image Contrast against | CT Image | CT Image |
| --- | --- | --- | --- |

| | Contrast (%) | | glandular (%) | Contrast-1 | Contrast-2 |
|---|---|---|---|---|---|
| keV | 5 mm | 10 mm | 10 mm | (HU) | (HU) |
| 20 | 10.65 | 21.30 | 8.20 | 263 | 100 |
| 22 | 8.25 | 16.51 | 6.51 | 262 | 103 |
| 24 | 6.50 | 13.01 | 5.08 | 254 | 100 |
| 26 | 5.25 | 10.51 | 4.03 | 238 | 91 |
| 28 | 4.37 | 8.74 | 3.36 | 218 | 83 |
| 30 | 3.72 | 7.45 | 2.90 | 198 | 76 |
| 32 | 3.22 | 6.44 | 2.53 | 182 | 71 |
| 34 | 2.82 | 5.64 | 2.22 | 171 | 66 |
| 36 | 2.51 | 5.02 | 1.97 | 163 | 64 |
| 38 | 2.27 | 4.53 | 1.76 | 158 | 60 |
| 40 | 2.08 | 4.15 | 1.60 | 154 | 59 |

CT image contrast-1 is the carcinoma against 50%/50% glandular and adipose;
CT image contrast-2 is the carcinoma against 100% glandular.

Initially, the volume scanning speed will be limited by the maximum frame rate of a real time FPD. The current available real time FPD has a frame rate of 30–60 frames/sec. However, flat panel researchers predict that the future frame rate can be up to 120 frames/sec. (1K×1K pixels/frame) and 480 frames/sec with reduced vertical readout lines (256×1K pixels/frame). When the frame rate of the detector is increased to 480 frames/sec. in the future, the volume scanning time of the breast will be shortened to 1–2 seconds depending on the required resolution, and/or the projection number can be increased to improve image quality. The FPD-based CBVCTBI scanner represents a significant technological advancement due to using a flat panel detector, slip ring technology, and cone beam reconstruction algorithms that result in accurate reconstruction.

There are three types of electronic imaging area detectors: fluorescent screen-CCD area detectors (FS-CCD), image intensifier-CCD (II-CCD) detectors and flat panel detectors (FPD). A comparison of the three current large area detectors is shown in Table 2 below. As shown in Table 2, the FS-CCD detectors have only 5% to 10% DQE. That results in image noise that is significantly greater on an equivalent radiation dose basis than that achieved by a modern helical CT scanner. Image intensifiers can achieve a 50% or higher DQE within the diagnostic radiation range and can offer much better low-contrast resolution on an equivalent radiation dose basis than FS-CCD based volume imaging systems.

TABLE 2

Comparison of Three Different Area Detectors (new table for detector)

| DETECTOR TYPE | DQE | DISTORTION | DYMAMIC RANGE | SPATIAL RESOLUTION (MM) | POSSIBLE FRAME RATE (UNITS) | VEILING GLARE |
|---|---|---|---|---|---|---|
| FS-CCD | 5–10% | No | 2000–4000:1 | 0.5 | 60 (512 × 512 × 12 bits) | No |
| II-CCD | 50–80% | 'S' & pincushion | 2000–4000:1 | 0.25–0.5 | 60 (512 × 512 × 12 bits) | Yes |
| TFT-FPD | 50–80% | No | >30,000:1 | 0.05–0.25 | 60 (512 × 512 × 16 bits) | No |

TABLE 3

The Desired Parameters of FPD for CBVCTBI

| Detector Type | DQE | Distor-tion | Dynamic Range | Spatial Resolution (mm) | Possible Frame Rate (Units) | Exp Range ($\mu$R) |
|---|---|---|---|---|---|---|
| Desired-FPD | 60–80% | No | 3,000:1–30,000:1 | 0.07–0.25 | 60–120 (512 × 512 × 16 bits) | 1–30,000 |
| Current-FPD | 60% | No | 3,000:1 | 0.25 | 30 (760 × 960 × 16 bits) | 1–3,000 |

However, an II-CCD-based system has some disadvantages such as bulky size, which is not suitable for CBVCTBI, limited dynamic range (1000–3000:1), geometric distortion (pincushion and S distortions) and veiling glare, which limit further improvement in low-contrast and spatial resolution. Therefore, an FPD is preferred. The FPD can be a thin-film transistor array FPD which can acquire both static digital images (radiographic images) and dynamic images (real-time acquisition). Table 3 shows the comparison between the desired parameters of FPD and the current parameters of FPD. Another preferred detector is any area detector with a resolution better than 1 lp/mm and an acquisition rate better than 2 frames per second which can acquire both static digital images and dynamic images.

Developing and optimizing an x-ray scatter control and reduction technique is one big challenge for CBVCTBI because CBVCTBI is less immune to scatter than fan-beam CT. CBVCTBI image contrast is reduced by scatter without an effective control technique. Scatter can be countered with a hybrid technique that uses an air gap technique to control scatter and a practical software correction technique for detected scatter. One of the major differences between fan beam slice CT and CBVCTBI is x-ray beam collimation. Using very narrow slit collimation in fan beam CT reduces scatter-to-primary ratio (SPR) to 0.2 or less. On the other hand, using a large cone collimation in cone beam geometry for mammography with only an air gap technique results in an average SPR up to 1 for average breast thickness. To minimize patient dose, an antiscatter grid is not used for an average size breast. A software correction technique is used to correct for detected scatter and to reduce overall average SPR to 0.2 or less. Convolution filtering techniques and scatter detected by the FPD are used to estimate scatter distribution and then subtract it from the total projection. A known convolution filtering technique taught in Love, L. A., and Kruger, R. A., "Scatter estimation for a digital radiographic system using convolution filter," *Med. Phys.* 1987; 14(2):178–185, was implemented for an image intensifier-based imaging system and produced an average percentage error of 6.6% for different anatomy and different clinical applications. That is equivalent to a reduction of SPR by a factor of up to 14. Even better scatter correction results can be achieved for an FPD-based system because there is no veiling glare component, compared to an II-based system where that is a more dominant component. Based on previous studies and preliminary results, it is anticipated that the average SPR in each cone beam projection can be reduced to 0.2. That is the equivalent SPR achievable in a fan beam slice CT, using a hybrid scatter correction technique (software correction plus air gap). That analysis and the preliminary results show that with the above-noted x-ray scatter reduction and correction techniques, the FPD-based CBVCTBI system provides more than adequate low contrast resolution for breast cancer detection.

The preferred embodiment combines an air gap technique with an antiscatter grid and a software correction technique for residual scatter. A 10–15 cm air gap technique is an effective method to prevent large angle scatter radiation from reaching the detector and to reduce average SPR to less than 1. It is contemplated that in the CBVCT system, the distance from the rotation center to the detector will be 20 cm. With that geometry, the air gap is more than 15 cm to achieve an average SPR less than 1.

The residual scatter present within the projection images is removed based on a convolution-filtering method or interpolation methods to estimate residual scatter distribution in each projection image. In the convolution filtering method, residual scatter is modeled as a low pass, spatially filtered version of the total projection (scatter plus primary). After estimating residual scatter in each projection, the residual scatter radiation is then subtracted to obtain primary distribution for reconstruction. That technique effectively reduces SPR from 1.0 to 0.2 or less. Appropriate techniques are taught in the inventor's co-pending patent application Ser. No. 10/078,529, filed Feb. 21, 2002.

Figure 5A:
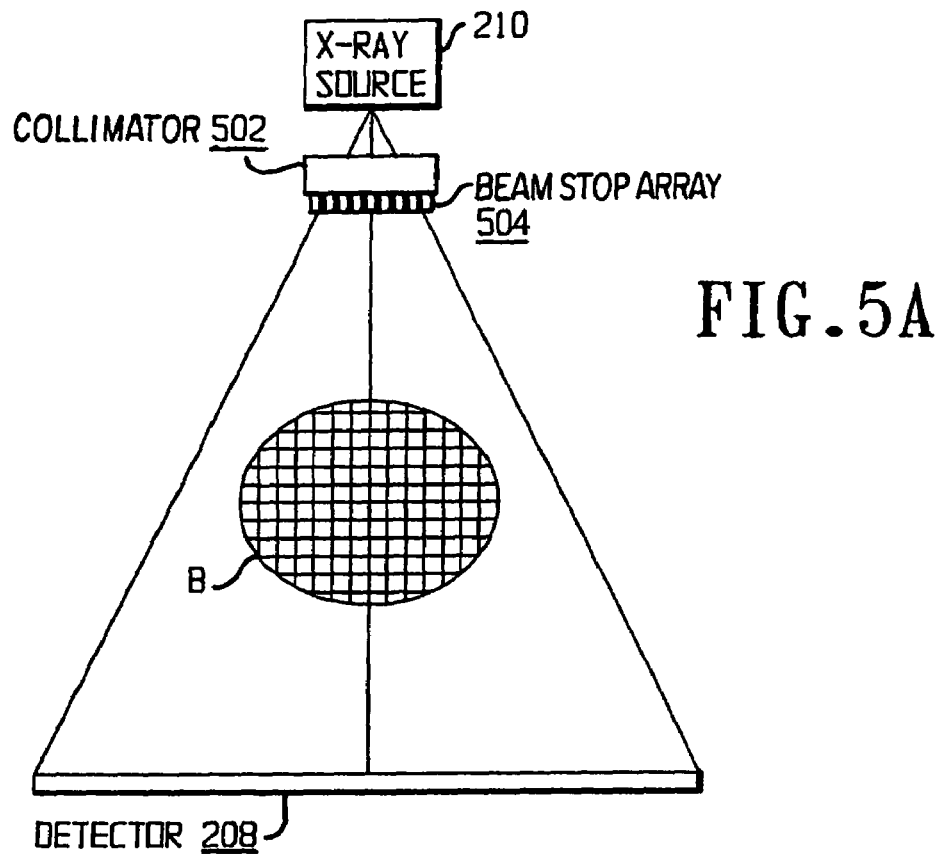
FIGS. 5A and 5B show a setup for taking scout images for scatter correction.
Figure 5B:
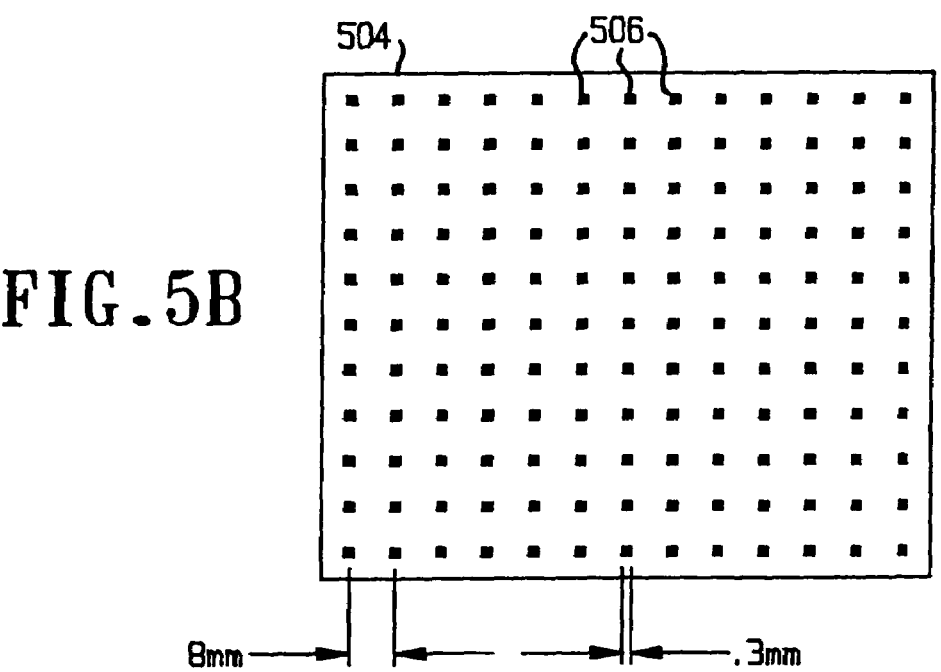

The conventional convolution filtering method requires two x-ray projections at each projection angle to accurately estimate residual scatter: one with a beam stop array for calculating two scaling factors and another without the beam stop array. That is not practical and would significantly increase patient dose in CBVCTBI. To overcome those difficulties, the preferred embodiment uses scout images for estimating scatter distribution in "real time" for each patient. Before starting to scan, one scout projection image is acquired, as in a standard fan beam CT. Traditionally, the scout images are used for positioning, and surveying body size to adjust the x-ray exposure levels in real time and reduce patient dose (as with 'Smart Scan™' in a GE helical CT). Before acquiring scout images, as shown in FIGS. 5A and 5B, a square matrix 504 of small lead ball bearings 506 is placed between the x-ray collimator 502 and the breast B. Both primary and sampled scatter distributions are estimated from the scout images with the lead beam stop array. The estimated primary images are used for a scouting purpose. The scaling factors for estimating scatter distribution and the convolution kernels at sampled angle positions can be determined. Then the scatter distributions are estimated using the convolution kernel at corresponding angle positions and subtracted from the detected projections. To reduce radiation dose to the patient P and computation load, only a minimum number of required scout images are acquired. Only one or two scout images are needed because after being lightly compressed, the breast has a cylindrical shape and when convolution filtering is applied to different anatomy, the accuracy of the method is not highly dependent on the exact shape of the convolution kernel, so long as its dimensions are large enough.

The exponential kernel is used for the estimation of residual scatter because a 2D exponential kernel is an optimum formation. The same 2D exponential kernel is used for all the projections since after being compressed, the breast has a cylindrical shape and the scatter distribution is almost unchanged with angle positions.

Another technique which can be used in the present invention to improve detection of breast tumors is the ultra-high-resolution volume-of-interest (VOI) reconstruction mode, which is analogous to magnified mammography. That technique can be used to focus on a suspicious lesion.

It is known in the art for flat panel detectors to have zoom modes. One source of such flat panel detector is Varian Imaging Products of Mountain View, Calif., U.S.A.

The zoom mode of a flat panel detector such as a Varian flat panel detector is used to acquire projection data for ultra-high VOI reconstruction. In the zoom mode, the detector can acquire a random block of 768×960 pixels at 30 frames/sec. with the full 4 lp/mm resolution of the sensor. The pixel size of the detector is 127 $\mu$m. A dual-focus spot x-ray tube is used, having focus spots of 0.1 and 0.3 mm. Ultra-high-resolution VOI can use a 0.3 mm focus spot, so that the focus spot size will not be a limiting factor of the spatial resolution for the VOI mode. Therefore, the FOV (field of view) of the zoom mode is 9.75×12.2 cm. To reduce unnecessary radiation to the patient P, a collimator limits the radiation to within the ROI (region of interest) in the VOI acquisition. A narrow strip of collimation (~2 cm wide) is needed. If the breast is larger than 12.2 cm in diameter, the projection data acquired in ultra-high VOI mode are truncated in the lateral direction. There are some streak artifacts if the reconstruction is obtained from the truncated data without preprocessing the data. The conventional method to deal with truncated projection data is to tail the projection data with a cosine wave before filtering. Fortunately, in the present case, the complete information in the region out of VOI is already available from the previous lower resolution scan. That information can be used to tail the truncated projection data and then complete the VOI reconstruction. Computer simulation indicates that such an algorithm eliminates the reconstruction artifacts introduced by truncated data within VOI. Such a technique is anticipated to be better than the conventional method. It is further anticipated that the ultra-high-resolution VOI reconstruction technique can provide up to 5.0 lp/mm resolution with a justifiable increase of the x-ray dose. The above-disclosed VOI technique can be used to detect other cancers, such as lung cancer.

Another use for CBVCTBI is in detecting volume growth. One known indicator of malignancy is rapid growth of the tumor. Since benign tumors are characterized by lack of growth, monitoring the rate of change of the volume growth of a tumor can identify whether it is malignant and in need of immediate removal. The accurate assessment of volume growth rate of tumors can be used to predict the doubling time of the tumor and is very helpful for physicians to make diagnostic and treatment decisions.

A volume of interest is scanned, and a 3D reconstruction matrix is obtained. Then an automatic detection algorithm is used to detect tumors, and a 3D segmentation is performed on all the detected tumors. Once the 3D segmentation is completed, the volume for each tumor is determined by counting all the voxels that are determined to belong to the tumor in the segmentation procedure. A known software package to perform such functions is the "ANALYZE" 3D display software package with 3D segmentation software. Volume growth can be determined by performing the same procedure at different times and comparing the volume.

Volume growth measurement is significantly more sensitive than diameter growth because volume changes as a function of the cube of the diameter. The proportional change in the breast tumor volume is much greater than the proportional change in the tumor diameter. Thus, a CBVCTBI-based volume growth measurement technique more accurately determines the change of a breast tumor, compared to conventional mammography which is only able to estimate the diameter change when the change is relatively large.

Figure 6A:
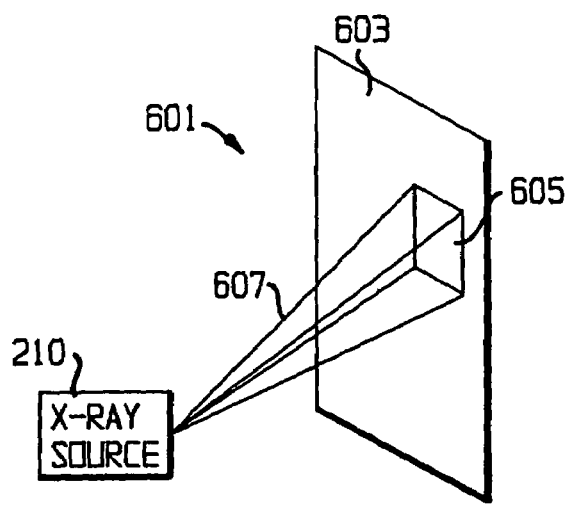
FIGS. 6A–6C show schematic diagrams of a dynamic collimator for use with the scanner of FIGS. 2A–2F.
Figure 6B:
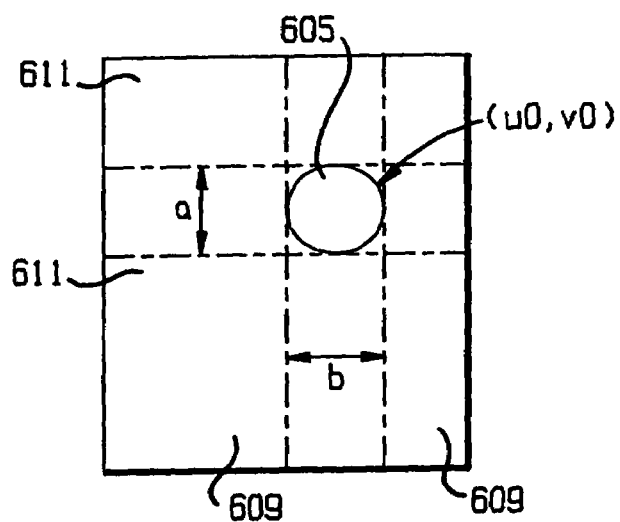
Figure 6C:
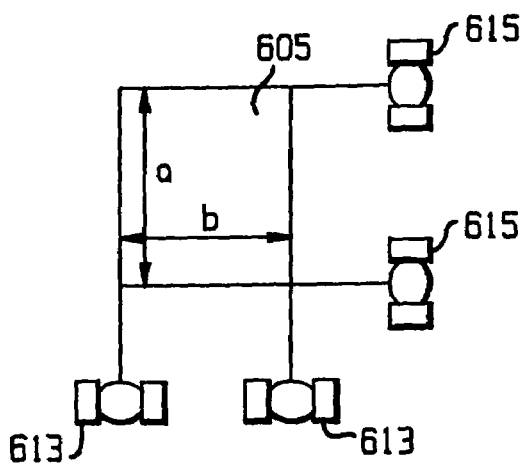

FIGS. 6A–6C show a dynamic collimator 601 usable with CBVCTBI in any of the embodiments disclosed above. The dynamic collimator can be used to reduce unnecessary radiation to a patient P while acquiring routine projection data for routine CBVCTBI reconstruction and/or ultrahigh spatial resolution projections for VOI reconstruction. The dynamic collimator 601 includes a collimator body 603 of lead or another suitable material with an aperture 605 therein for admitting only a desired portion 607 of the x-rays emitted by the x-ray source 210. The collimator body 603 can be formed in any suitable manner, but it is preferably formed with two lead leaves 611 spaced apart by a distance a and two lead leaves 609 spaced apart by a distance b. Thus, the aperture 605 has a rectangular shape of dimensions a×b. Stepper motors 613, 615 move the collimator body 603 in two orthogonal directions to center the aperture 605 on coordinates (u0, v0) corresponding to the center of the volume of interest. With the collimator 601, x-rays radiate only the ROI for routine CBVCTBI reconstruction and/or ultrahigh resolution acquisition, and routine CBVCTBI reconstruction images and/or ultrahigh resolution reconstruction images can be obtained. The stepper motors 613, 615 also control the spacing between each pair of leaves so that a and b can be varied.

Experimental results indicate that the smallest carcinoma detectable using CBVCTBI is 1–2 mm in diameter and the smallest calcification is 0.2 mm in diameter with the equivalent radiation dose of 240 mRad for an average breast size (10–12 cm around chest wall) and reconstruction voxel size of 0.36 mm. The results imply that with the total dose level less than that of a single screening mammography exam (assuming two views are required for each breast) for an average size breast, CBVCTBI imaging is able to detect a few millimeter carcinoma and 0.2 mm calcification. With such a radiation dose level and such detectibility, the patient benefit-to-risk ratio can be over 800:1.

Other advantages of the invention will now be explained with reference to FIGS. 8A, 8B and 9A–9C.

CBVCTBI provides the ability to form three-dimensional images, while traditional mammography is limited to two dimensions. Such separation would be impossible in a two-dimensional image.

Figure 8A:
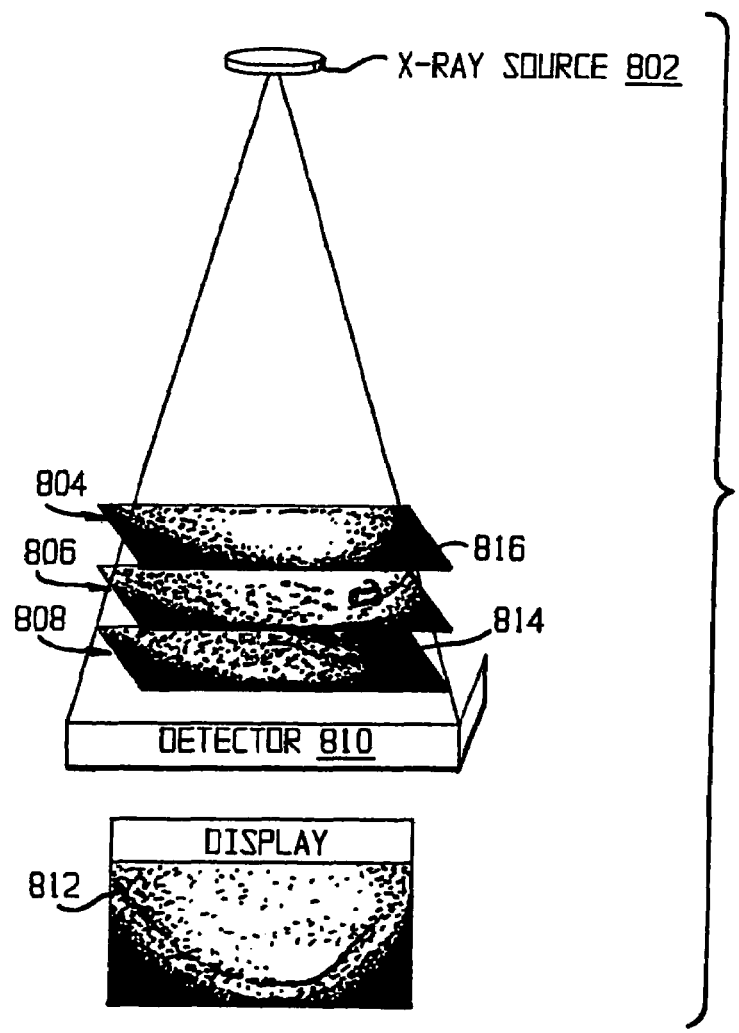
FIG. 8A shows a problem in conventional mammography techniques in which a lesion in one plane cannot be separated from another object in another plane.

More specifically, as seen in FIG. 8A, a conventional mammography technique uses an x-ray source 802 to image planes 804, 806 and 808 of the breast on a detector 810. The resulting two-dimensional display, shown as 812, always has an overlap problem and consequently has limited sensitivity and specificity of breast carcinoma detection. More specifically, a lesion 814 in plane 808 cannot readily be distinguished from an overlapping other object 816 in plane 806.

Figure 8B:
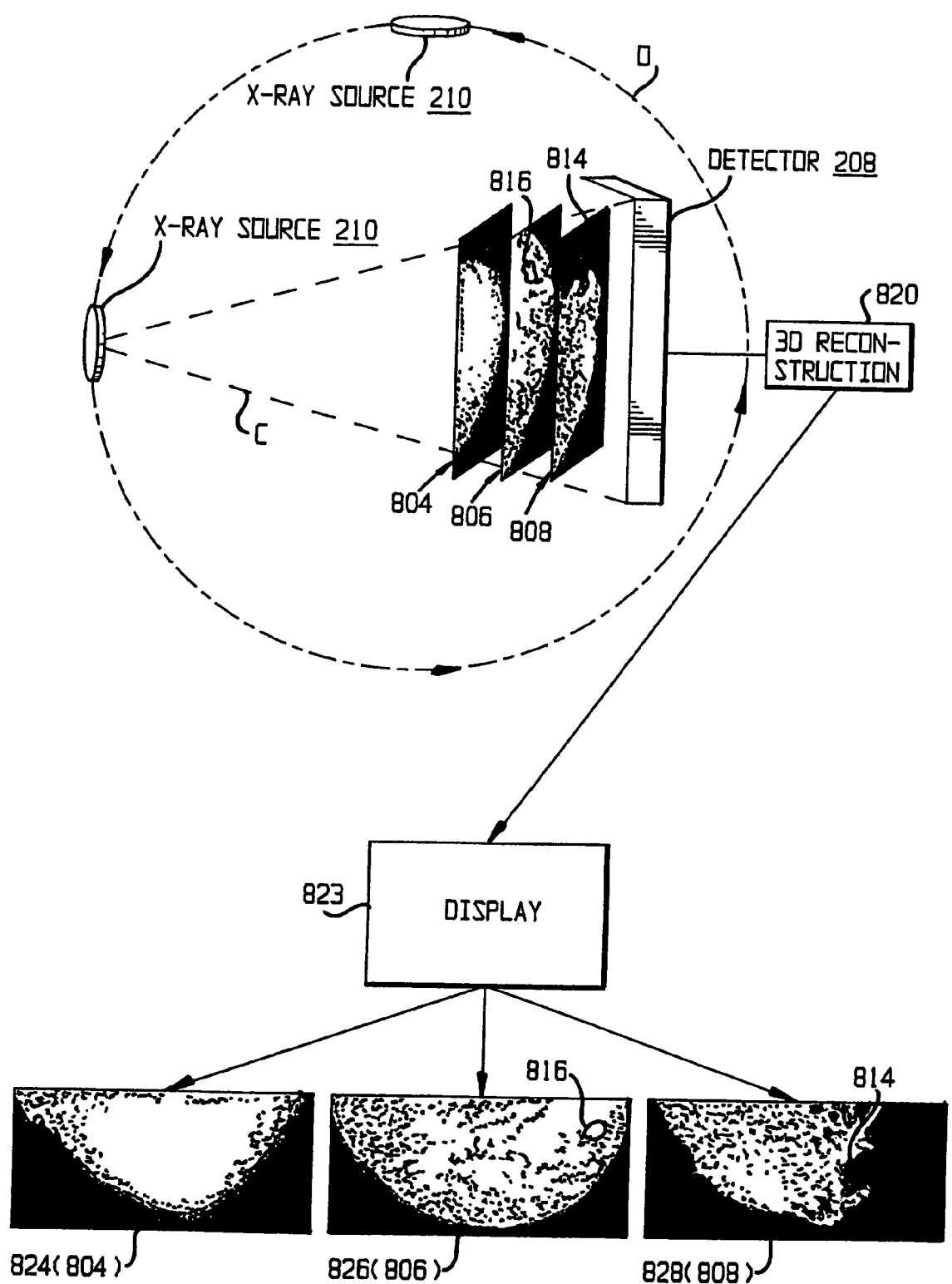
FIG. 8B shows the separation of a lesion in one plane from another object in another plane, in the CBVCTBI reconstruction image.

By contrast, as shown in FIG. 8B, CBVCTBI provides a three-dimensional image including separate imaging of the planes 804, 806 and 808. After the three-dimensional reconstruction step 820 and the display step 822, the three planes 804, 806 and 808 are imaged in separate images 824, 826 and 828. Thus, the lesion 814 can be isolated from the overlapping other object 816. Accordingly, CBVCTBI reconstruction images isolate superimposed planes and significantly improve the sensitiviey and specificity of breast carcinoma detection compared with the conventional projection mammography of FIG. 8A.

Of course, the showing of only three planes is for illustrative purposes and should not be construed as limiting the invention.

Figure 9A:
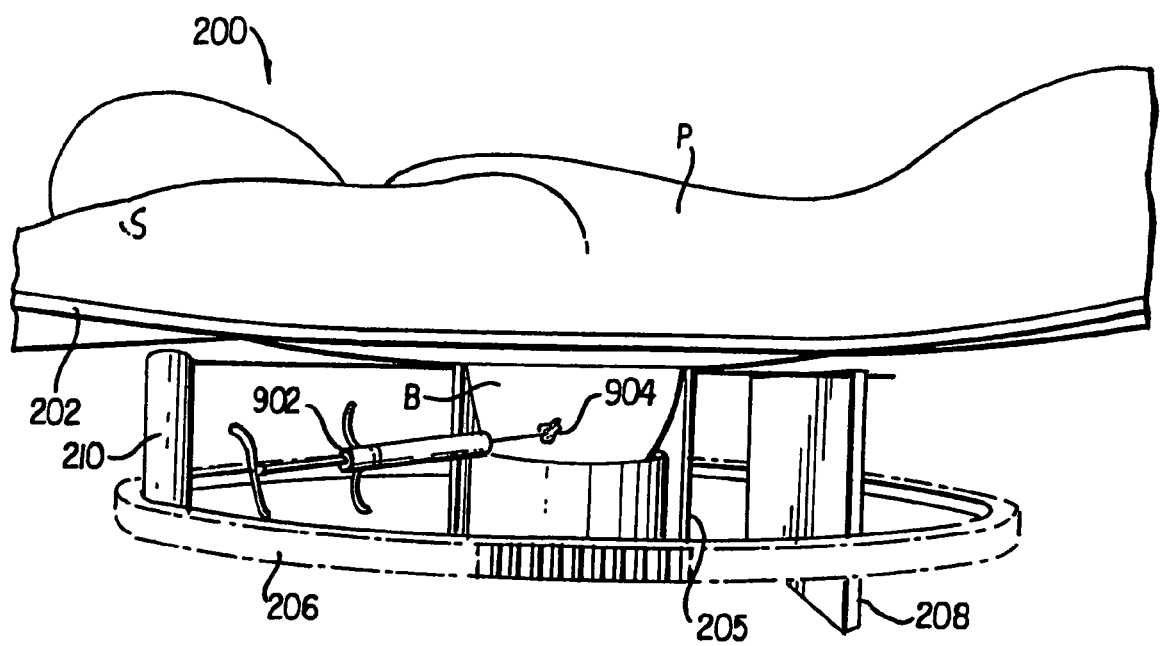
FIG. 9A shows a use of the three-dimensional CBVCTBI scanner in guiding a needle during a biopsy.
Figure 9B:
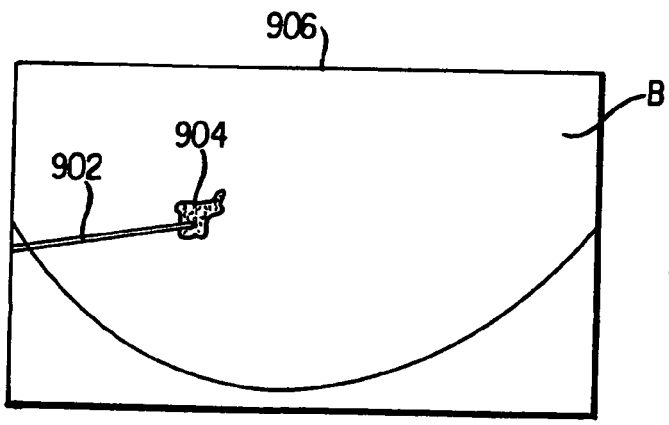
FIG. 9B shows a real-time two-dimensional image taken with the scanner of FIG. 9A.
Figure 9C:
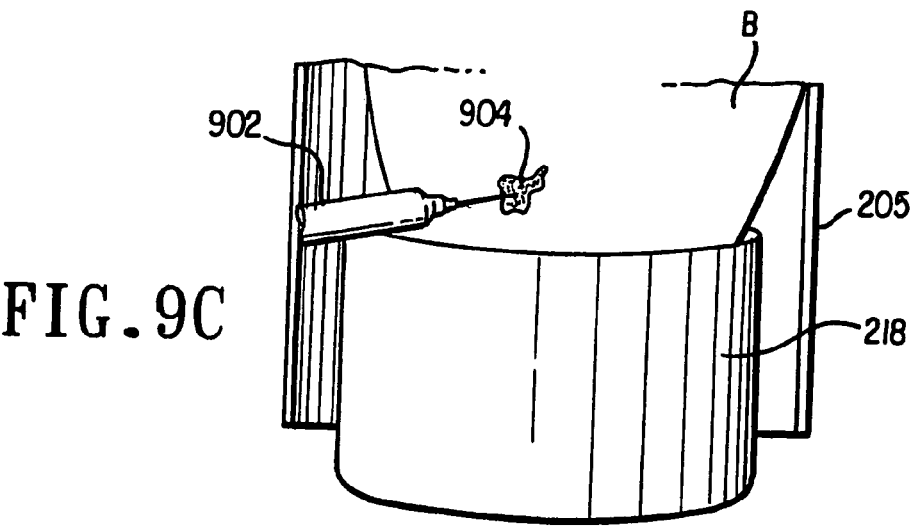
FIG. 9C shows image fusion of two-dimensional real-time images such as that of FIG. 9B with three-dimensional reconstruction.

Further, three-dimensional imaging can be used in image guided biopsy techniques. For example, as shown in FIG. 9A, the scanner 200 is used to guide a biopsy needle 902 to a lesion 904 in the patient P's breast B. FIG. 9B shows a real-time two-dimensional image taken with the scanner 200, in which the biopsy needle 902 and the lesion 904 are shown in the breast B. FIG. 9C shows image fusion of two-dimensional real-time images such as that of FIG. 9B with three-dimensional reconstruction. With the three-dimensional reconstruction of FIG. 9C, the biopsy needle 902 can be guided toward the lesion 904 in three dimensions.

Figure 10:
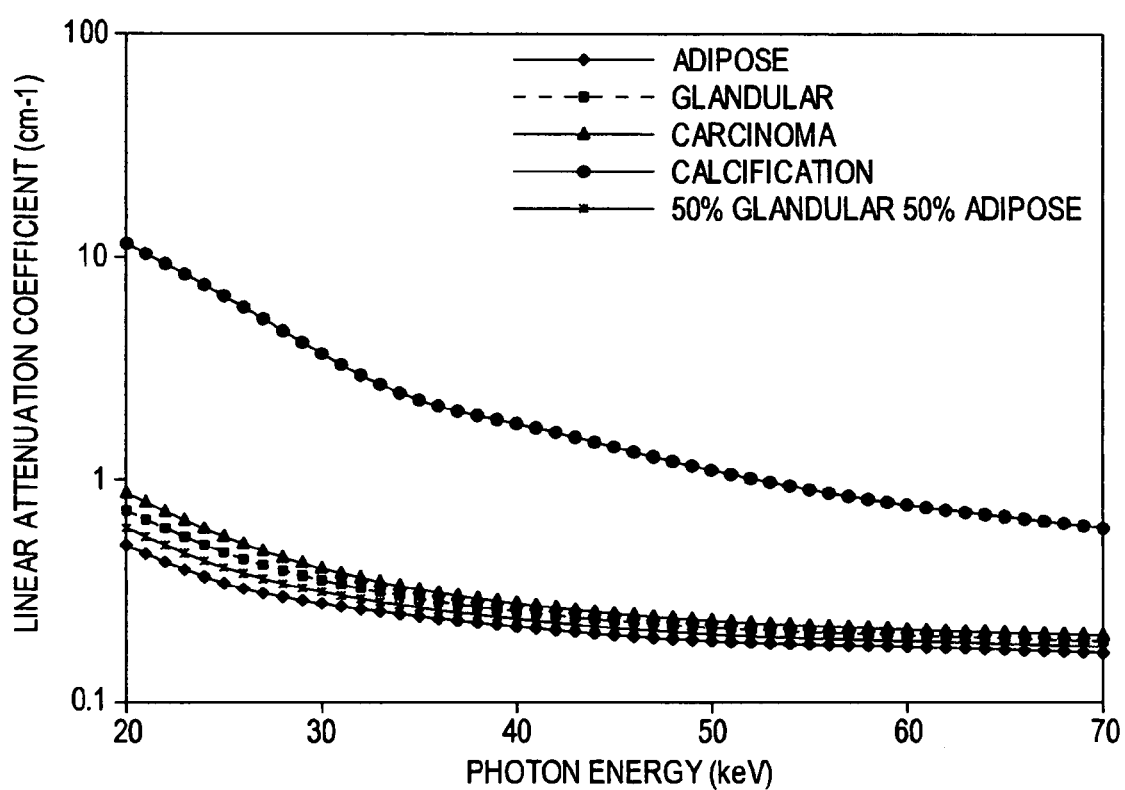
FIG. 10 shows plots of linear attenuation coefficients of various tissues and lesions obtained from a materials library.

A material library, storing x-ray attenuation characteristics of various tissues and materials, can be used to improve calculations. The library can be stored in a computing device as a look-up table or in any other suitable format. With the material library, the inventor obtained the plot of FIG. 10, which delineates how the x-ray linear attenuation coefficients of five kinds of breast tissue and lesions, namely adipose, glandular, base material (e.g. mixture of 50% adipose and 50% glandular), carcinoma and calcification, change with various photon energy levels. The value for calcification is much larger than that for other materials, which means the extremely high relative contrast of calcification would enable the detection of small spots of a hundred micrometers in size despite an observable brightness spread. Notice that when the keV is lower, the values for base material (e.g. mixture of 50% adipose and 50% glandular) and other soft tissues are significantly different from each other. However, when the keV is higher, the differences become much less prominent. Clearly, the normal x-ray technique for CT (e.g. 120 kVp and 300 mA) is not suitable for breast imaging, as happened in the early CTM, since sufficient contrast is necessary for soft tissue imaging and an improper technique would jeopardize the contrast needed for lesion detection.

Three more variations of the preferred embodiment will now be disclosed.

One such variation of the CBVCTBI scanner, shown in FIGS. 11A and 11B, is to allow a patient P to first stand up on a step 1102 when the table 1100 is at an upright position, as shown in 11A. Then, by adjusting the vertical position of the step using a computer or manually controlled motor 1104 or 1106, the patient P's breast will be positioned at the center of the hole 1108 in the table. During this procedure, the patient P will be wrapped (not shown) to prevent the patient P from moving and the table will be transited to the horizontal position for exam, as shown in FIG. 11B. It may be more convenient to position the patient P using this feature.

Figure 12A:
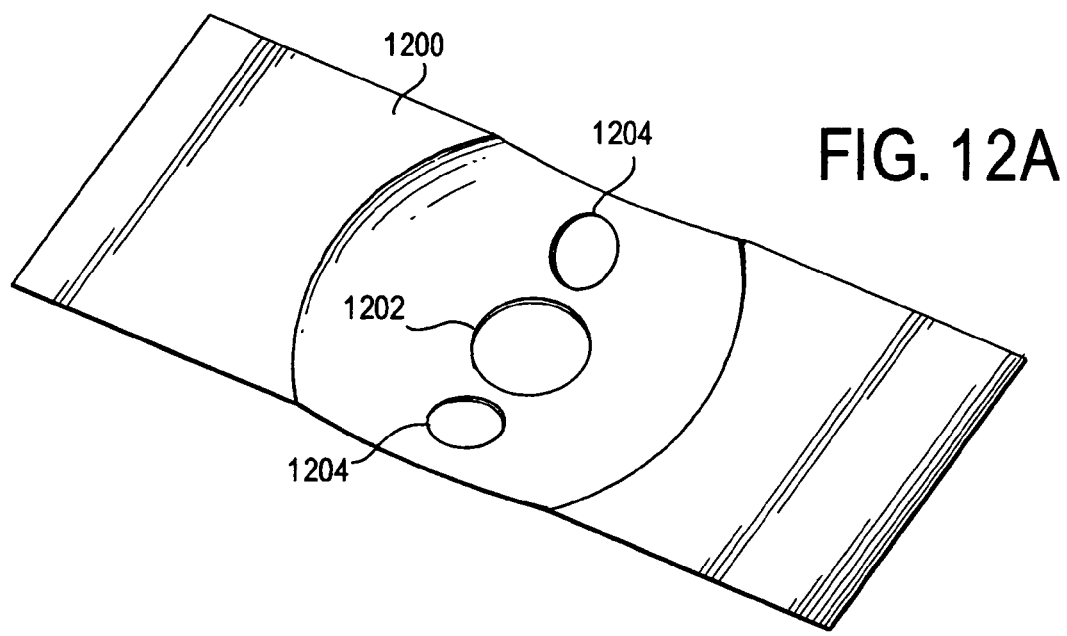
FIGS. 12A–12D show another modification of the scanner.
Figure 12B:
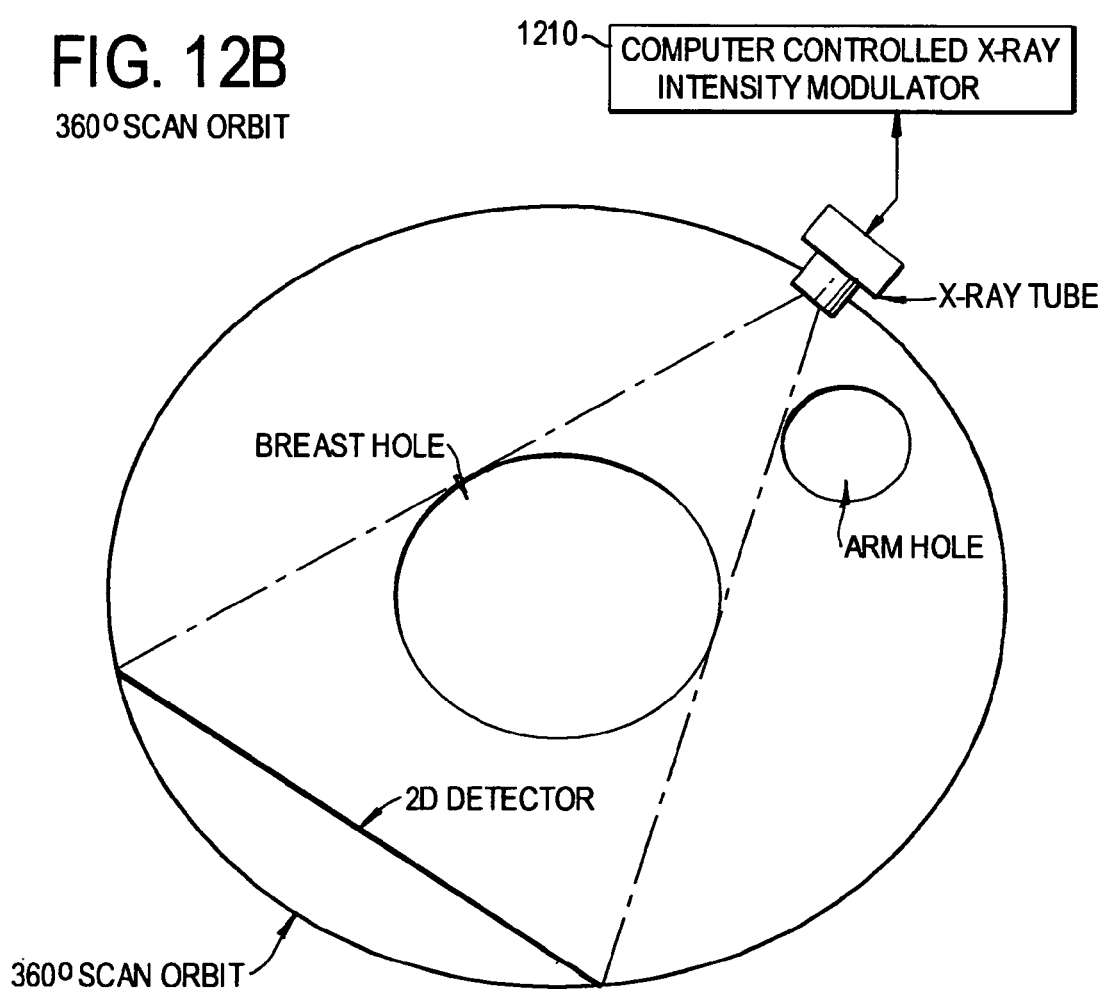
Figure 12C:
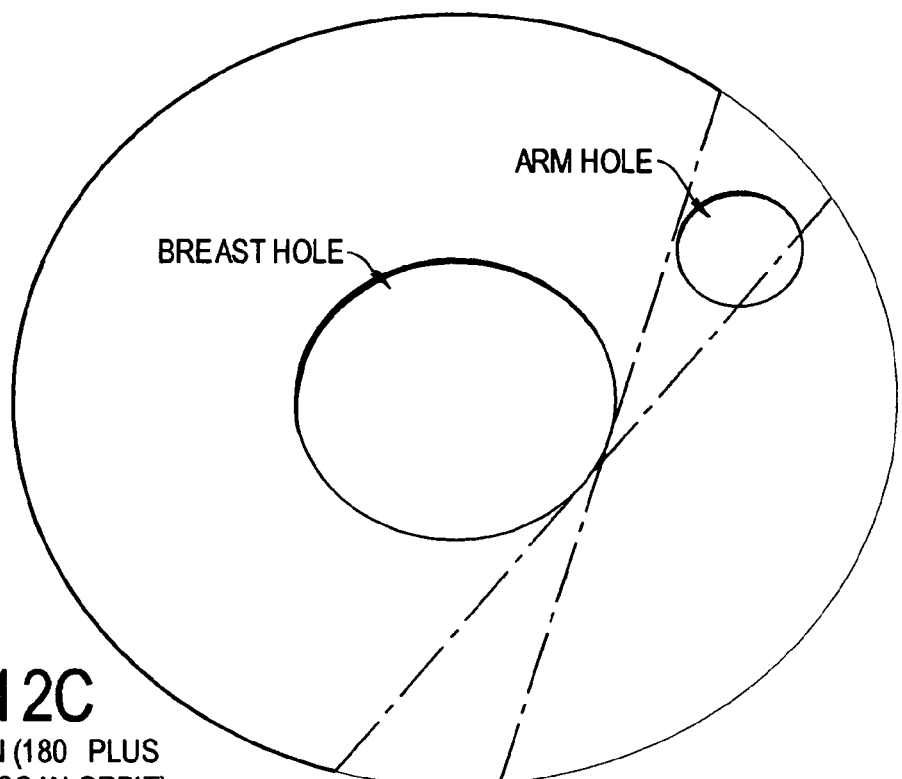
Figure 12D:
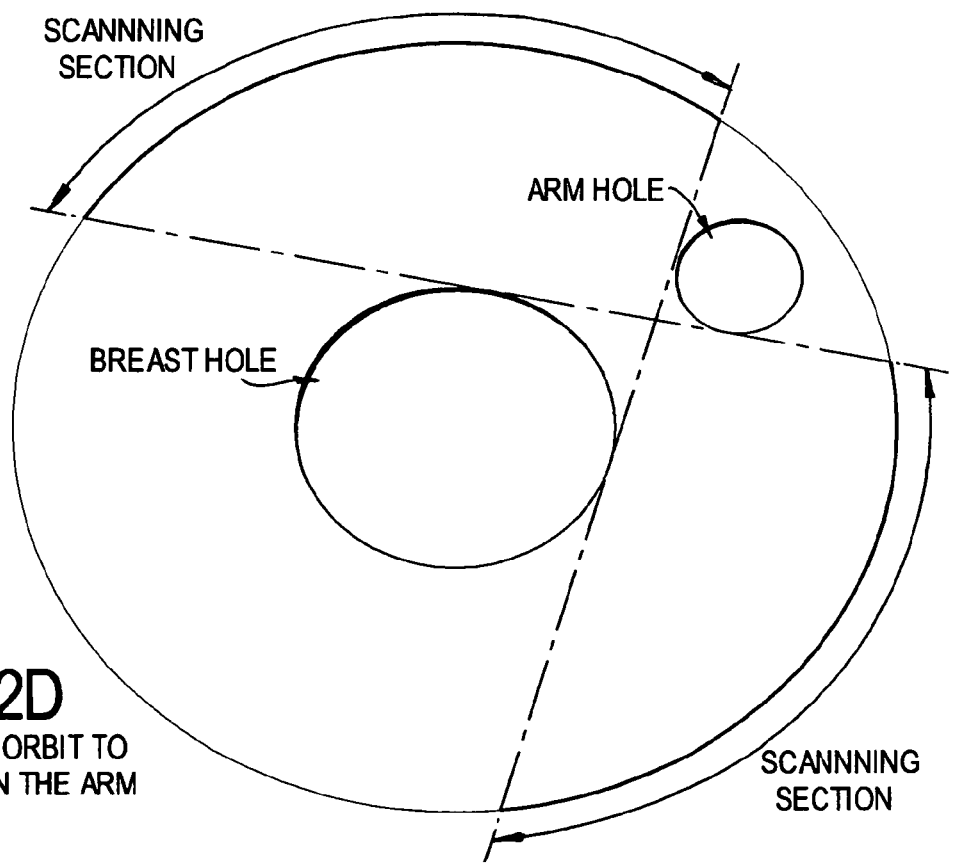

Another variation of CBVCT breast-imaging scanner is to build a patient table so that there are multiple holes through the table and the center of one hole 1202 is at the rotation center for the breast to be scanned, as shown FIG. 12A. Another hole or holes 1204 are to the side or sides of the breast hole 1202 to allow the patient P's hand to drop down naturally. In this way, appropriate coverage of the chest wall of the breast for some patients can be achieved. In this version, the scan protocols and reconstruction algorithms may be different from that without dropping down the arm. FIG. 12B shows a 360° scan orbit using a computer-controlled x-ray intensity modulator 1210 that reduces the radiation dose to the patient P while achieving the uniform image quality of projections, and then reconstruct the whole breast and arm using the reconstruction algorithms:. Wang X. and Ning R., "A cone beam reconstruction algorithm for a circle-plus-an arc acquisition geometry," IEEE Trans Med Imag, 1999: vol. 18(9), 815–824, Tang X and Ning R. "A cone beam filtered back-projection (CB-FBP) reconstruction algorithm for a circle-plus-two-arc orbit," Med. Phys. 28 (6):1042–1055, (2001), Hu H. "A new cone beam reconstruction algorithm and its application to circular orbits" SPIE 1994; 2163:223–234, and/or Wang G, Liu Y, Cheng PC "Half-scan cone-beam x-ray microtomography formula", Scanning Vol. 16, 216–220 (1994). The algorithms in the articles just cited are given as illustrative rather than limiting. Any other suitable algorithms can be used instead The reader's attention is directed to U.S. Pat. Nos. 5,999,587, 6,075,836, 6,298,110, 6,477,221, 6,480,565 and 6,504,892, all by the present inventor. The computer-controlled x-ray modulator (shown in FIG. 12B) modulates x-ray intensities to the patient P during projection acquisition according to the variation of patient thickness by increasing or decreasing the x-ray tube current (mA) or tube voltage (kVp) or both mA and kVp. Alternatively, as shown in FIG. 12C, an 180-degree-plus-cone-angle scan orbit can be used. Another option is to perform a partial scan (as shown in FIG. 12D) without scanning the arm and reconstruct the breast from the partial scanned projection data using an iterative reconstruction algorithm:. Chen Z, and Ning R "Accurate Perspective Projection Calculation Using a Pixel-Pyramid Model in Flat Panel Detector-Based Iterative Cone Beam Reconstruction", SPIE MI2003, Feb. 16, 2003, San Diego. The algorithms in the articles just cited are given as illustrative rather than limiting. Any other suitable algorithms can be used instead; the reader's attention is directed to U.S. Pat. Nos. 5,999,587, 6,075,836, 6,298,110, 6,477,221, 6,480,565 and 6,504,892, all by the present inventor.

Still another variation of the CBVCT breast-imaging scanner is to scan both breasts within one scan, as shown in FIGS. 13A and 13B. The table 1300 has two breast holes 1302; otherwise, it can be configured like the table of FIGS. 11A and 11B or in any other suitable manner. This version will incorporate computer-controlled collimation to shape the x-ray beam such that only breast tissue will be covered. The table has two breast holes and can be moved laterally and longitudinally to position a breast at the rotation center a time for scan to reduce the time of reposition of the patient P and improve throughput. In this version of the table, the scanning protocol and reconstruction algorithms can be the same as the ones with only one breast hole.

Figure 13C:
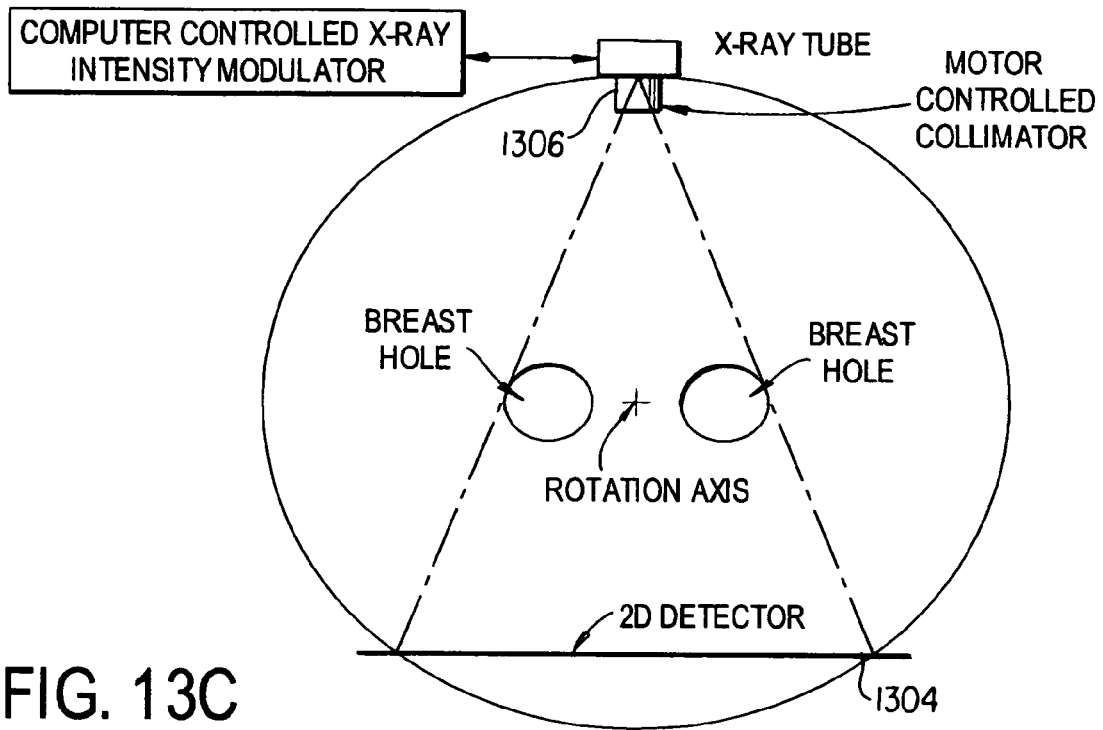

Another proposed version of the CBVCT breast-imaging scanner, using the table of FIGS. 13A and 13B, is to scan both breasts within one scan with a computer-controlled x-ray modulator that reduces the radiation dose to the patient P while achieving the uniform image quality of projections. The patient table is not required to move between the scans for the same patient P. This version will incorporate computer-controlled collimator 1306 (please see FIG. 13C) to shape the x-ray beam such that only breast tissue will be covered. For this version, the size of the detector 1304 will be sufficiently large to cover both breasts within a single scan. The computer-controlled x-ray modulator modulates x-ray intensities to the patient P during projection acquisition according to the variation of patient thickness by increasing or decreasing the x-ray tube current (mA) or tube voltage (kVp) or both mA and kVp. The following reconstruction algorithm can be used to reconstruct the two breasts: Wang X. and Ning R., "A cone beam reconstruction algorithm for a circle-plus-an arc acquisition geometry," IEEE Trans Med Imag, 1999:vol. 18(9), 815–824 and Tang X and Ning R. "A cone beam filtered back-projection (CB-FBP) reconstruction algorithm for a circle-plus-two-arc orbit," Med. Phys. 28 (6):1042–1055, (2001) or Hu H. "A new cone beam reconstruction algorithm and its application to circular orbits", SPIE 1994; 2163:223–234. The algorithms in the articles just cited are given as illustrative rather than limiting. Any other suitable algorithms can be used instead; the reader's attention is directed to U.S. Pat. Nos. 5,999,587, 6,075,836, 6,298,110, 6,477,221, 6,480,565 and 6,504,892, all by the present inventor.

Figure 14C:
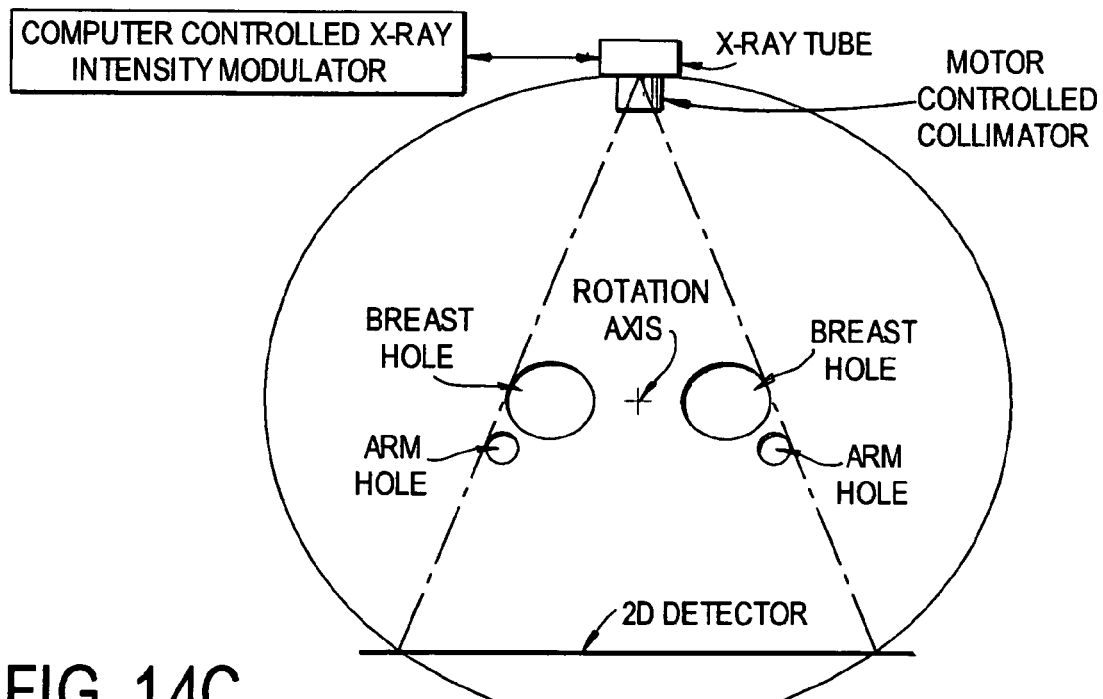

Another proposed version of the patient table of the CBVCT breast-imaging scanner is shown in FIGS. 14A and 14B. During the scan, both computer-controlled collimator and computer-controlled x-ray intensity modulator are used in the same way as discussed above (See FIG. 14C). The table 1400 has four holes 1402, 1404, of which two inner holes 1402 are breast holes and two outer holes 1402 allow the patient P to drop an arm naturally during scanning. In this version, the patient table can be moved laterally and longitudinally to position a breast at the rotation center a time for scan to reduce the time of reposition of the patient P and improve throughput while an arm drops naturally during the scan to achieve appropriate coverage of the chest wall of the breast for some patients. In this version of the table, the scanning protocol and reconstruction algorithms can be the same as the ones with only one breast hole and arm hole.

Another version of the CBVCT breast-imaging scanner is to scan both breasts within one scan while both arms can be drop down naturally to allow appropriate coverage of breast tissue at the chest wall, as shown in FIGS. 14A and 14B. Unlike the previous version, the patient table is not required to move between the scans for the same patient. During the scan, both computer-controlled collimator and computer-controlled x-ray intensity modulator are used in the same way as discussed above (See FIG. 14C). There are four holes through the table and the center of the table is at the rotation center. Two inner holes are for the breasts to be scanned, as shown FIG. 14B. Two outer holes are to the side of the former to allow the patient P's hand to drop down naturally, as shown in FIGS. 14A and 14B. In this way, appropriate coverage of the chest wall of the breast for some patients can be achieved. In this version, the scan protocols and reconstruction algorithms may be different from that without dropping down the arm. One option is to perform a partial scan (as shown in FIG. 12D) without scanning the arm and reconstruct the breast from the partial scanned projection data using an iterative reconstruction algorithm:. Chen Z, and Ning R "Accurate Perspective Projection Calculation Using a Pixel-Pyramid Model in Flat Panel Detector-Based Iterative Cone Beam Reconstruction", SPIE MI2003, Feb. 16, 2003, San Diego. The algorithms in the articles just cited are given as illustrative rather than limiting. Any other suitable algorithms can be used instead; the reader's attention is directed to U.S. Pat. Nos. 5,999,587, 6,075,836, 6,298,110, 6,477,221, 6,480,565 and 6,504,892, all by the present inventor. Another option is to use the scan protocols shown in FIG. 12B or FIG. 12C to scan both the breasts and the arms with x-ray intensity modulator and then reconstruct the whole breasts and arms using the reconstruction algorithms:. Wang X. and Ning R., "A cone beam reconstruction algorithm for a circle-plus-an arc acquisition geometry," IEEE Trans Med Imag, 1999:vol. 18(9), 815–824 and Tang X and, Ning R. "A cone beam filtered back-projection (CB-FBP) reconstruction algorithm for a circle-plus-two-arc orbit," Med. Phys. 28(6): 1042–1055, (2001), Hu H. "A new cone beam reconstruction algorithm and its application to circular orbits", SPIE 1994;2163:223–234 or Wang G, Liu Y, Cheng PC. "Half-scan cone-beam x-ray microtomography formula", Scanning Vol. 16, 216–220 (1994). The algorithms in the articles just cited are given as illustrative rather than limiting. Any other suitable algorithms can be used instead; the reader's attention is directed to U.S. Pat. Nos. 5,999,587, 6,075,836, 6,298,110, 6,477,221, 6,480,565 and 6,504,892, all by the present inventor.

Figure 15A:
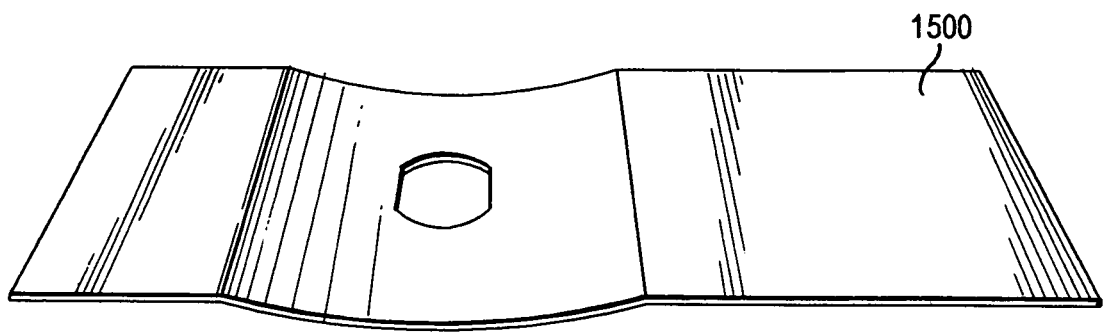
FIGS. 15A–15C show the use of a wedge to assist the positioning of the patient to improve coverage of the breast and the chest wall.
Figure 15B:
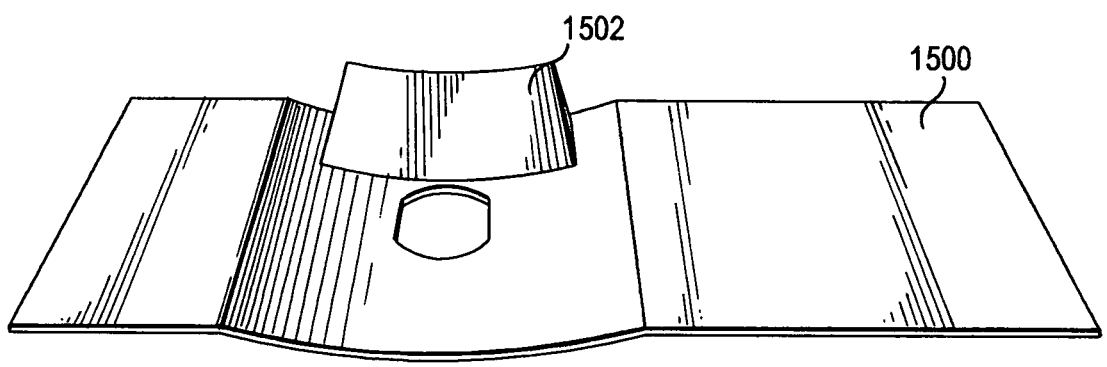
Figure 15C:
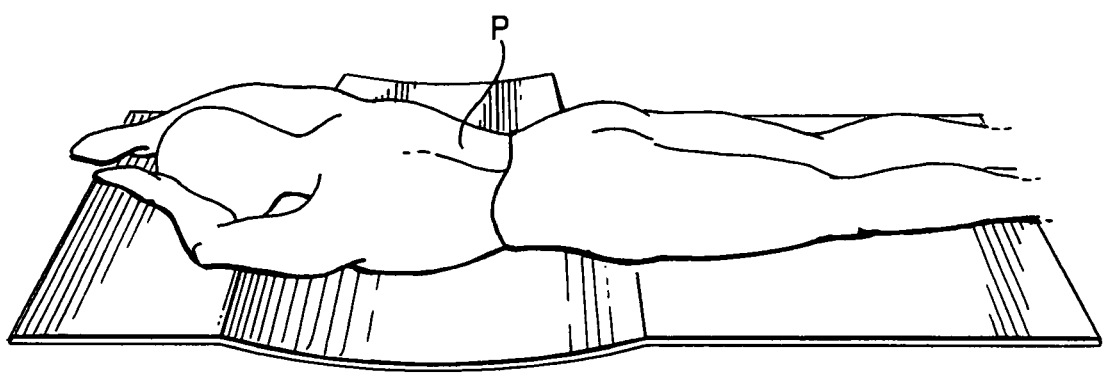

Another version of the CBVCT breast-imaging scanner, as shown in FIGS. 15A and 15B, is to scan a breast a time with a wedge 1502 on the patient table 1500. The purpose of using the wedge 1502 is to rotate the patient P's body counterclockwise slightly when the left breast is scanned or clockwise slightly when the right breast is scanned, respectively, to achieve an appropriate coverage of chest wall of a breast during a CBVCTBI scan. The use of the wedge with a patient P is shown in FIG. 15C. In this case, the patient table can be the any version of the patient table that allows to scan a breast a time, discussed in this application and in U.S. Pat. No. 6,480,565. Although both the hands of the patient P are shown as upward in FIG. 15C, it is preferred that at least the left hand of the patient P be put downward aside the body on the table when the left breast of the patient P is scanned, and at least the right hand be downward aside the body on the table when the right breast is scanned, respectively.

While a preferred and variations thereof have been set forth above in detail, those skilled in the art who have reviewed the present disclosure will readily appreciate that other embodiments are possible within the scope of the present invention. For example, radiation other than x-rays can be used. Also, image analysis techniques such as those taught in U.S. Pat. Nos. 5,999,587, 6,075,836, 6,298,110, 6,477,221, 6,480,565 and 6,504,892 (all by the present inventor), whose disclosures are hereby incorporated by reference, can be used. Therefore, the present invention should be construed as limited only by the appended claims.

What is claimed is:

1. A device for producing an image of a breast of a patient, the device comprising:
   a gantry frame;
   at least one motor for moving the gantry frame to form a data acquisition geometry in which image data are taken;
   a source of a beam of radiation attached to the gantry frame to move with the gantry frame;
   a two-dimensional (2D) digital detector attached to the gantry frame to move with the gantry frame, the 2D digital detector being disposed in a path of the beam of radiation; and
   a table on which the patient rests while the image data are taken, the table supporting the patient such that the breast is disposed between the source of cone-beam radiation and the 2D digital detector, the table having a hole through which the breast extends and being configured such that an entirety of the breast extending through the hole is in the path of the beam of radiation;
   wherein the at least one motor moves the gantry frame so that the 2D digital detector takes a volume scan of the breast; and
   wherein the table has a second hole to permit an arm of the patient to drop through the second hole while the volume scan is taken.

2. The device of claim 1, wherein the device performs a scan geometry to avoid the patient's arm.

3. The device of claim 1, wherein the at least one motor moves the table laterally and longitudinally relative to the gantry to reposition the patient for a new scan.

4. The device of claim 1, further comprising an intensity modulator to reduce the radiation dose to the patient while achieving the uniform image quality of projections.

5. The device of claim 4, further comprising a computer-controlled collimator for reducing a radiation dose to the patient.

6. The device of claim 1, wherein the table has two breast holes and two arm holes.

7. The device of claim 6, wherein the at least one motor moves the table laterally and longitudinally relative to the gantry to reposition the patient for a new scan.

8. The device of claim 6, wherein the gantry frame and the table are configured such that the volume scan is taken of both of the patient's breasts in a single scan.

9. The device of claim 6, wherein the detector is sized to scan both of the patient's breasts in a single scan.

* * * * *